US011096750B2

(12) United States Patent
Mayer-Ullmann et al.

(10) Patent No.: US 11,096,750 B2
(45) Date of Patent: Aug. 24, 2021

(54) JOINT ASSEMBLY, GUIDING DEVICE, MANUFACTURING AND USE OF A JOINT ASSEMBLY

(71) Applicant: Karl Storz SE & Co. KG, Tuttlingen (DE)

(72) Inventors: Gregor Mayer-Ullmann, Munich (DE); Jordi Hogervorst, Ueberlingen (DE); Andre Ehrhardt, Wurmlingen (DE)

(73) Assignee: Karl Storz SE & Co. KG, Tuttlingen (DE)

( * ) Notice: Subject to any disclaimer, the term of this patent is extended or adjusted under 35 U.S.C. 154(b) by 671 days.

(21) Appl. No.: 15/388,984

(22) Filed: Dec. 22, 2016

(65) Prior Publication Data
US 2017/0181803 A1    Jun. 29, 2017

(30) Foreign Application Priority Data
Dec. 23, 2015    (DE) .......................... 102015122802.5

(51) Int. Cl.
    *B33Y 80/00*      (2015.01)
    *B25J 17/02*      (2006.01)
         (Continued)

(52) U.S. Cl.
    CPC .............. *A61B 34/35* (2016.02); *A61B 90/11* (2016.02); *B25J 17/0283* (2013.01);
         (Continued)

(58) Field of Classification Search
    CPC ................... B25J 17/0283; G05G 9/47; G05G 2009/04707; A61B 90/11; A61B 34/35
    See application file for complete search history.

(56) References Cited

U.S. PATENT DOCUMENTS

| | | | | |
|---|---|---|---|---|
| 675,106 | A | * | 5/1901 | Oberle ...................... F16L 3/26 248/49 |
| 892,105 | A | * | 6/1908 | White ..................... F16L 3/202 248/60 |

(Continued)

FOREIGN PATENT DOCUMENTS

| | | |
|---|---|---|
| CN | 102306471 A | 1/2012 |
| DE | 202009018442 U1 | 9/2011 |

(Continued)

OTHER PUBLICATIONS

European Search Report Application No. 16206688.0 Completed Date: May 23, 2017; dated May 31, 2017 7 pages.

(Continued)

*Primary Examiner* — Daniel D Yabut
(74) *Attorney, Agent, or Firm* — Whitmyer IP Group LLC

(57) ABSTRACT

A joint assembly for a guiding device comprises a plurality of guiding elements that are concentrically aligned with respect to one another and at least sectionally spherically shaped. The guiding elements are arranged as components of a combined spherical bearing and comprise spherical contact areas. At least two of the guiding elements are integrally manufactured. The at least two guiding elements enable a relative pivot movement therebetween. A guiding device for an instrument incorporates a respective joint assembly. A method of manufacturing a joint assembly involves integrally manufacturing at least to guiding elements that form components of a combined spherical bearing. Uses of a joint assembly involve a use as a spherical bearing in an instrument holder for a simulation system or an assistance system for minimally invasive operations.

20 Claims, 12 Drawing Sheets

(51) Int. Cl.
*A61B 34/35* (2016.01)
*A61B 90/11* (2016.01)
*B33Y 10/00* (2015.01)
*A61B 17/34* (2006.01)
*A61B 17/00* (2006.01)
*A61B 90/00* (2016.01)

(52) U.S. Cl.
CPC ............... *B33Y 10/00* (2014.12); *B33Y 80/00* (2014.12); *A61B 2017/0069* (2013.01); *A61B 2017/00526* (2013.01); *A61B 2017/3409* (2013.01); *A61B 2090/061* (2016.02); *A61B 2090/067* (2016.02); *A61B 2090/0813* (2016.02)

(56) References Cited

U.S. PATENT DOCUMENTS

| | | | | |
|---|---|---|---|---|
| 1,317,903 | A * | 10/1919 | Whimster | B60R 13/00 248/541 |
| 3,638,973 | A * | 2/1972 | Poletti | A61B 17/02 285/184 |
| 5,387,220 | A * | 2/1995 | Pisharodi | A61B 90/14 128/898 |
| 6,034,336 | A * | 3/2000 | Lee | H01H 25/04 200/18 |
| 6,109,815 | A * | 8/2000 | Merlo | F16C 11/106 403/103 |
| 6,217,249 | B1 * | 4/2001 | Merlo | F16C 11/0604 403/128 |
| 6,494,635 | B1 * | 12/2002 | Merlo | F16C 11/106 403/103 |
| 8,157,567 | B2 * | 4/2012 | Chen | G09B 23/285 434/262 |
| 2004/0101813 | A1 * | 5/2004 | Irion | G05G 9/047 434/262 |
| 2016/0003290 | A1 * | 1/2016 | Trotter | B60G 7/003 403/56 |
| 2016/0003292 | A1 * | 1/2016 | Trotter | B60G 7/001 403/134 |
| 2017/0209329 | A1 * | 7/2017 | Ishibashi | F16C 11/06 |
| 2018/0223897 | A1 * | 8/2018 | Bergner | F16H 59/02 |

FOREIGN PATENT DOCUMENTS

| | | |
|---|---|---|
| GB | 2503422 A | 1/2014 |
| WO | 0237452 A1 | 5/2002 |

OTHER PUBLICATIONS

German Search Report Application No. 10 2015 122 802.5 dated Oct. 5, 2016 12 Pages.

* cited by examiner

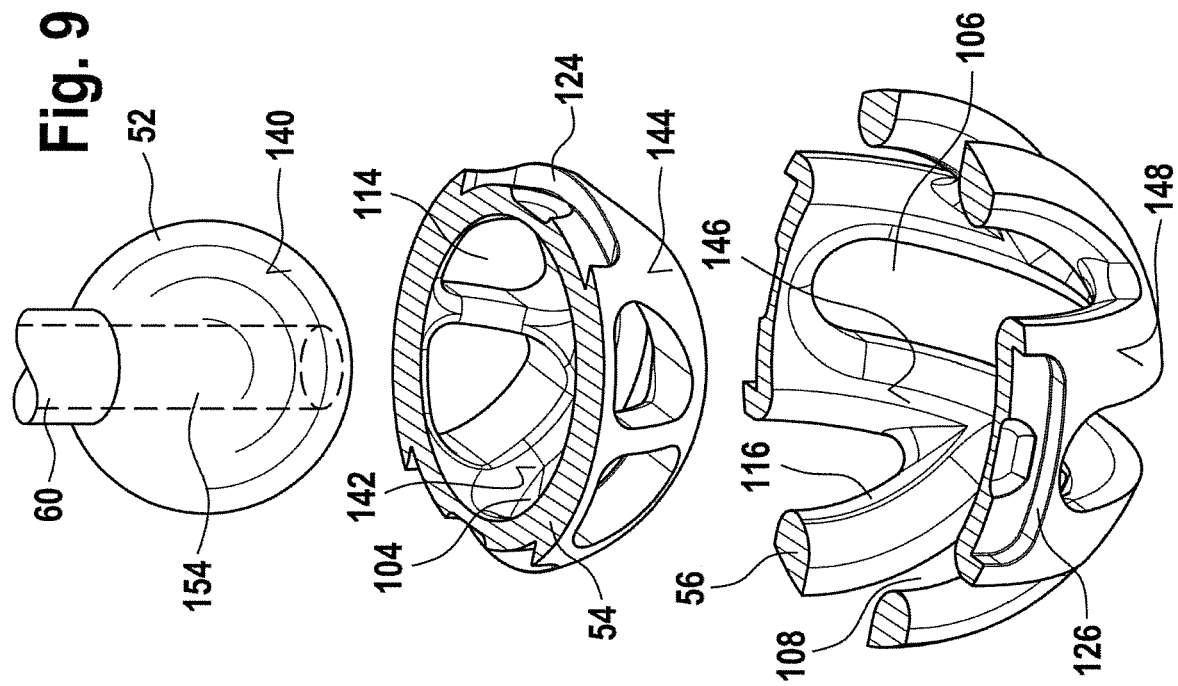
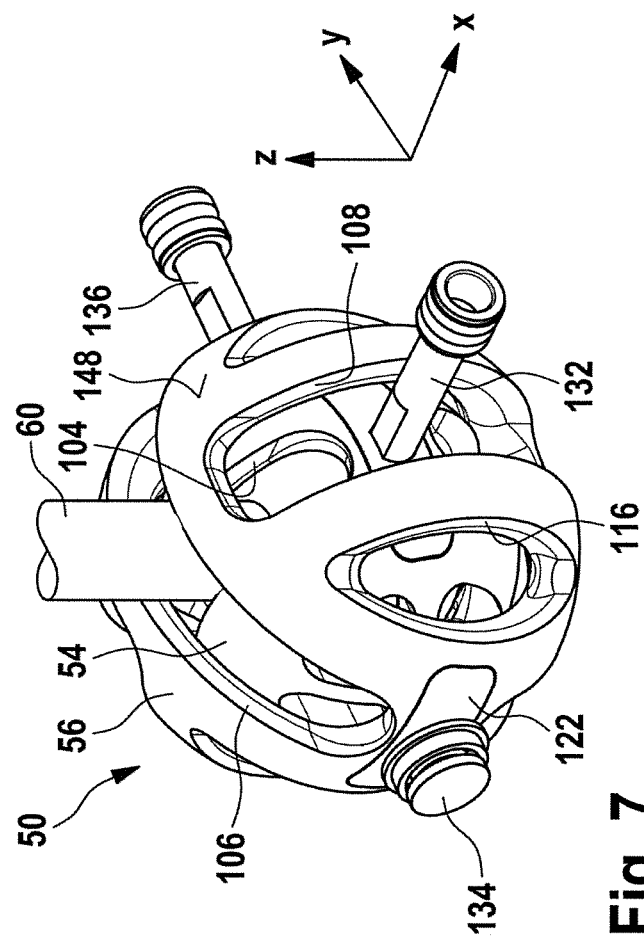
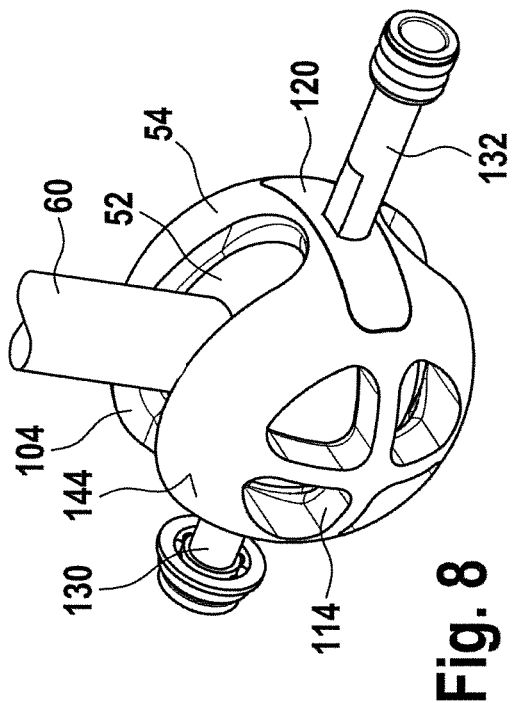

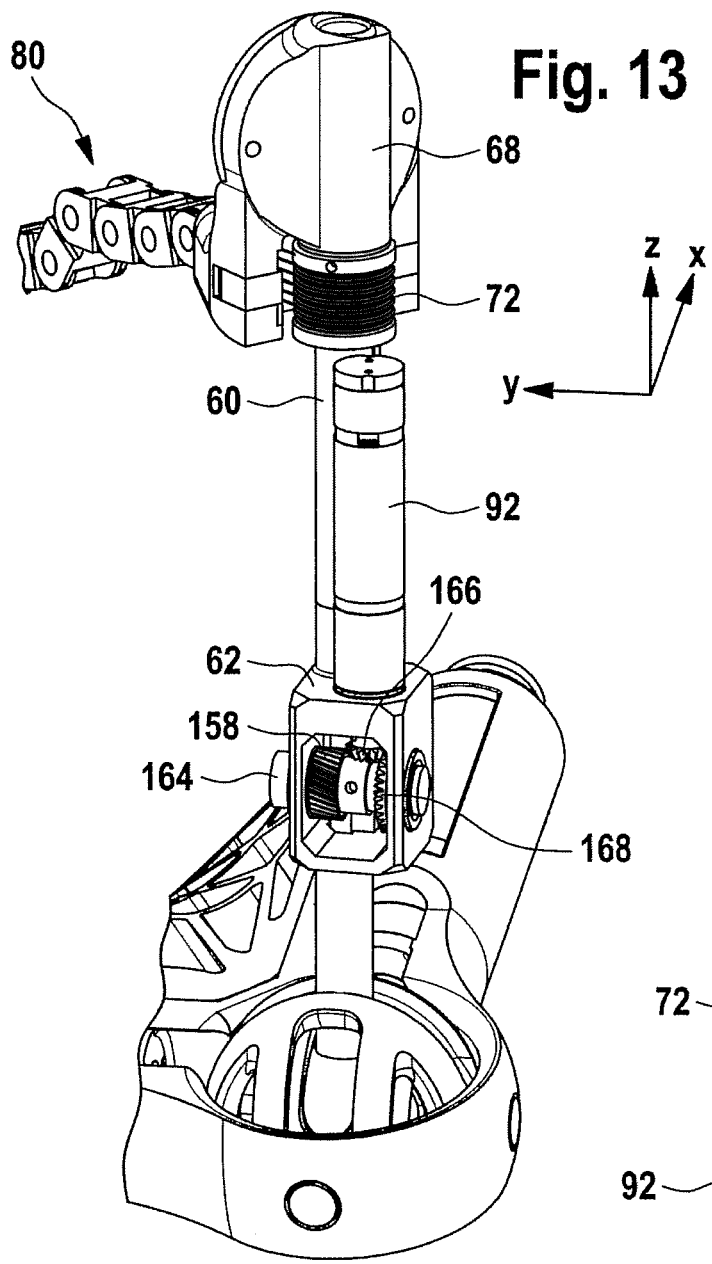
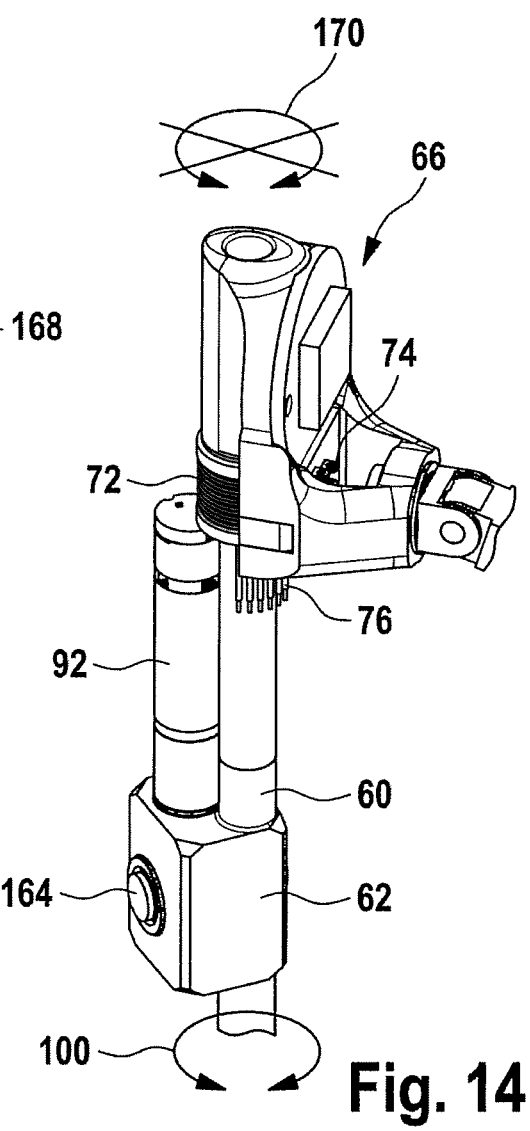

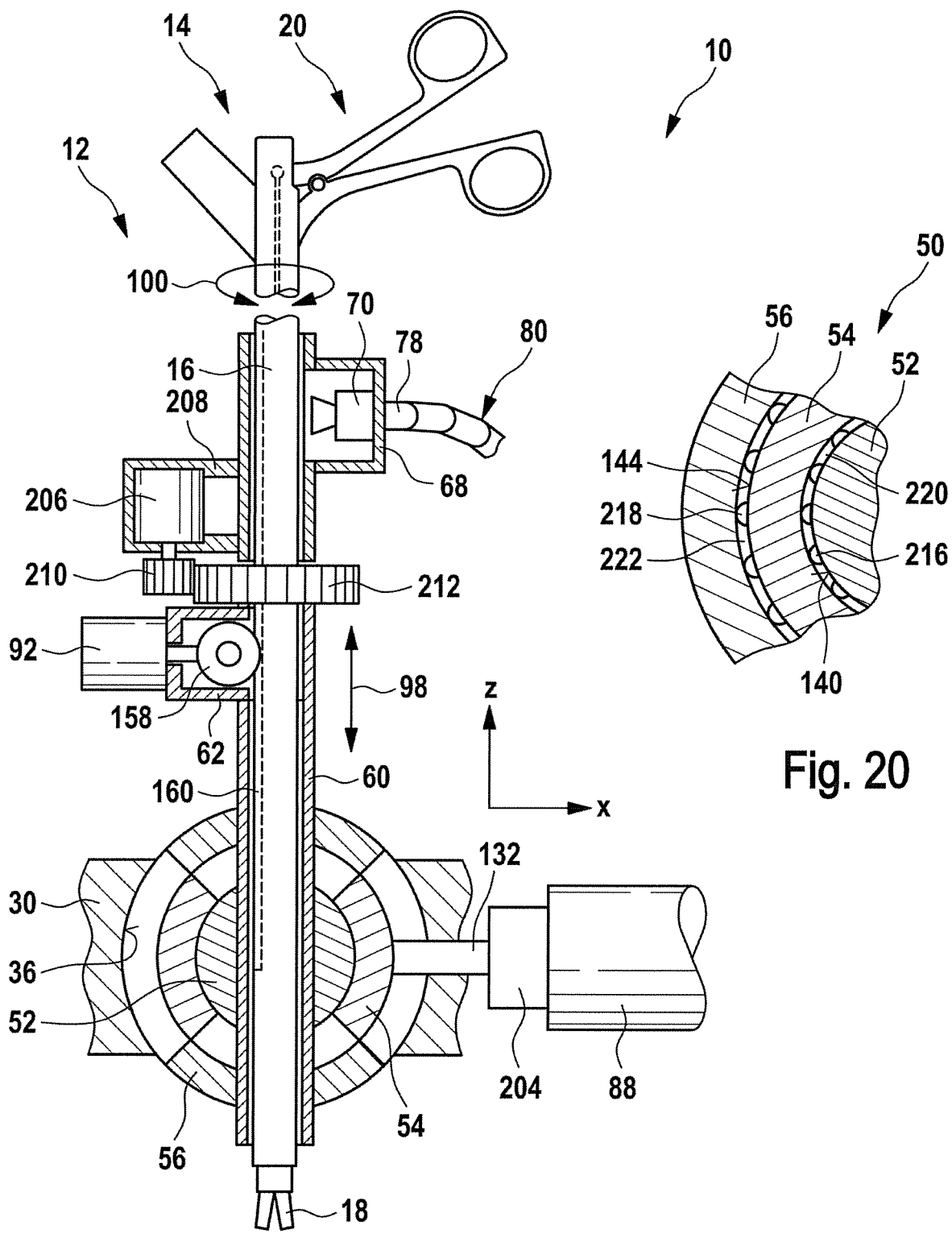

JOINT ASSEMBLY, GUIDING DEVICE, MANUFACTURING AND USE OF A JOINT ASSEMBLY

CROSS-REFERENCES TO RELATED APPLICATIONS

This application claims priority from German patent application 10 2015 122 802.5, filed on Dec. 23, 2015. The entire content of that priority application is fully incorporated by reference herewith.

BACKGROUND

The present disclosure relates to a joint assembly for a multi-axis-guiding device for an instrument, such as a medical instrument or a simulation instrument. The disclosure further relates to a guiding device comprising such a joint assembly and to the manufacture of a joint assembly. The disclosure further relates to exemplary uses of joint assemblies of this type.

US 2004/0101813 A1 discloses a holding device for a medical simulation apparatus that comprises a plurality of degrees of freedom of movement for an instrument that is provided with a longitudinal shaft, wherein the holding device comprises a gimbal mounting involving a ball-shaped element that is mounted rotatable about a first pivot axis and a second pivot axis, wherein the shaft of the instrument is partially accommodated in the ball-shaped element.

The afore-mentioned US 2004/0101813 A1 explicitly relates to apparatuses for simulating surgical operations, particularly minimally invasive operations. In addition, the use of such holding devices that are configured for supporting and guiding instruments for assistance systems for real medical operations may be envisaged. Hence, it may also be useful for real minimally invasive surgical operations when the instruments, particularly endoscopic instruments, are guided and mounted in a defined fashion. In this way, the handling effort for the operating surgeon may be reduced. A further field of application may be seen in the field of telemedicine, i.e. for diagnostic and/or therapeutic procedures, wherein for instance the operating surgeon may not act immediately (in terms of space) at the patient. Endoscopic instruments and simulation instruments generally involve a longitudinal shaft, wherein a tool, optics, and such like may be mounted to the distal end thereof.

A further field of application for such holding devices for instruments is for instance present in the context of technical diagnosis and/or quality assurance. Currently, the instruments may for instance be arranged as inspection devices, probes, measuring sensors, cameras, sensors and such like. In addition, generally also applicability in the field of manufacturing technology and/or material processing may be present. Accordingly, the instruments may be arranged as machining tools and/or processing tools.

The holding device disclosed in US 2004/0101813 A1 provides a guide for an instrument which is gimbal-mounted. Pivot axes of the gimbal bearing are coupled to actuators that are arranged to generate torques. In this way, a so-called force feedback feature may be provided, particularly for simulation applications. In this way, tissue may be simulated during the simulation of surgical operations that is contacted by the instrument that is currently operated by the operating surgeon. In this way, a feedback as to whether soft tissue, hard tissue or even cartilage tissue or bones are present may be provided to the operating surgeon.

However, it has been observed that holding device according to US 2004/0101813 A1 acquires certain manufacturing efforts and assembly efforts. This may limit the prevalence and application of such holding devices.

In view of this, it is an object of the present disclosure to provide an alternative multi-axis-guiding device for an instrument.

It is a further object of the present disclosure to present a joint assembly for a guiding device that is easy to manufacture. Preferably, at least in some embodiments, both manufacturing effort and also assembly effort may be reduced. It is desirable that this may be achieved without compromising the desired function.

It is a further object of the present disclosure to present a joint assembly and a guiding device that incorporates the joint assembly that are of compact design, to minimize the installation space requirements.

It is a further object of the present disclosure to present a method of manufacturing a joint assembly that achieves at least some of the afore-mentioned aspects.

It is a further object of the present disclosure to present exemplary uses of such a joint assembly, wherein the afore-mentioned aspects may have a positive effect on the operation.

SUMMARY

In regard of the joint assembly, these and other objects are achieved by a joint assembly for a multi-axis guiding device for an instrument, wherein the joint assembly comprises a plurality of guiding elements that are concentrically oriented with respect to one another and at least sectionally spherically shaped, wherein the guiding elements are arranged as components of a combined spherical bearing and comprise spherical contact areas, wherein at least two of the guiding elements are integrally manufactured, and wherein the at least two guiding elements enable a relative pivot movement.

The above aspect is based on the insight that, at least in some exemplary embodiments of the present disclosure, manufacturing the joint assembly may be significantly simplified when the guiding elements that form linkage elements are jointly manufactured, wherein the elements are directly arranged into one another during their production. In other words, no separate assembly of the guiding elements is necessary. The term integral manufacturing relates to a manufacturing in a joint state and/or an already assembled state. Preferably, the guiding elements form a spherical bearing comprising two non-parallel pivot axes. Generally, the two pivot axes are inclined by 90° with respect to one another. In this way, the joint assembly may provide the function of a gimbal bearing, for instance in accordance with the above-mentioned US 2004/0101813 A1. However, this may be achieved at a significantly smaller effort for single parts, manufacturing effort and assembly effort.

The guiding elements may also be referred to as spherical elements or ball section elements. Accordingly, the guiding elements are, in at least some embodiments, arranged as at least sectionally ball-shaped ball elements. This may involve complete or nearly completely shaped balls and/or spherical shells. However, also annular, ring-segment shaped, segment-shaped or segment-sectional shaped forms may be envisaged. As further elements are mounted to at least one of the guiding elements, the ball elements are at least partially provided with guiding recesses and such like.

The integral shape has the effect that, using only a single manufacturing procedure, eventually at least two parts may be manufactured that are movable with respect to one another, particularly arranged to be pivoted with respect to one another. In some embodiments, the guiding elements are arranged to be respectively pivoted (by a certain value) relative to one another about one of two pivot axes that intersect in the center of the join arrangement. Hence, ideally, a single, integrally manufactured (joint) component may form the joint assembly of the multi-axis guiding device. It is to be noted that further elements may be added, for instance to provide three or even more movement axes (corresponding to in total three or even more degrees of freedom of movement).

By way of example, movement axes and degrees of freedom of movement of the multi-axis-guiding device will be elucidated with reference to a Cartesian coordinate system (X-Y-Z). According to at least some embodiments, the joint assembly enables a defined pivot movement of the instrument about the X-axis and about the Y-axis that are oriented perpendicular to one another. Consequently, two movement axes and/or two degrees of freedom of movement are present. An extension of the multi-axis guiding device may be accomplished by a pivotability or rotatability of the instrument about the Z-axis that is perpendicular to the X-axis and perpendicular to the Y-axis. In this way, three movement axes and/or three degrees of freedom of movement are provided.

An extension of the multi-axis guiding device may for instance be achieved by a translational movability of the instrument along the Z-axis. In this way, in total four movement axes and/or four degrees of freedom of movement may be achieved. The four movement axes may involve three pivot axes and/or rotation axes (about the X-axis, Y-axis, Z-axis) and a translational axis for linear sliding movements (movements along the Z-axis).

In some embodiments, the at least two guiding elements of the joint assembly are obtained from an integral and additive manufacture from a Material that is arranged to be processed in an additive manufacturing process. It is further preferred that this applies in total to three guiding elements that are concentrically arranged in one another.

Plastic materials, metal materials but also ceramics and composites are suitable for additive manufacturing. An exemplary additive manufacturing process is the so-called 3D printing. Generally, 3D printing involves processing plastic materials; however, also the processing of metal materials may be envisaged. However, also further additive processes are known, for instance, stereolithography, selective laser sintering, selective laser melting, and such like. Additive manufacturing processes may be envisaged which enable also processing considerably harder and/or stiffer materials, for instance metal materials, ceramics and such like. Additive manufacturing processes may be operable single-stage, for instance with 3D printing, wherein the structure to be formed is directly printed. However, also multi-stage additive manufacturing processes may be envisaged, wherein for instance a blank part is formed in an additive procedural step, wherein the blank part subsequently undergoes a further procedural step, for instance a thermal processing step. It may be envisaged to form the guiding elements in an additive fashion from a base material into which an additional material is injected.

Two or more guiding elements that are concentrically arranged in one another may be formed through additive manufacturing procedures, wherein the guiding elements simply provide a multi-axis spherical bearing that may only be manufactured with very huge manufacturing efforts and assembly efforts by use of conventional manufacturing technologies.

In some embodiments, the joint assembly may be manufactured by use of the additive manufacturing procedures without or with only little finish processing. Additive manufacturing may be used to form components having tolerances that qualify for the use as spherical bearing in the indicated fields of application. It may be envisaged to apply a defined preloading to the components so that potentially remaining tolerances may be minimized to further improve the surface quality and/or the guiding quality.

According to a further embodiment of the joint assembly, at least one contact area is arranged at the at least to guiding elements that is provided with a plurality of protrusions. In exemplary embodiments, a nubby contact surface is arranged at the at least to guiding elements. This arrangement may considerably contribute to a reduction of the guiding clearance and to an increasing accuracy.

Generally, additive manufacturing procedures do not enable "zero-tolerances", as in this way solid components would eventually be produced. Hence, components that are nested in one another are generally provided with sufficient "clearance" to enable a separation of the single parts. In accordance with the above-mentioned aspect, for instance nubby protrusions are formed at at least one contact area so that the single parts (the guiding elements) may safely be separated from one another after the additive manufacture, i.e. may be pivoted with respect to one another. In other words, even though a defined clearance is formed between two neighboring guiding elements that are arranged in one another, at least selectively elevated elements are formed in this clearance that serve as contact elements between the guiding elements.

Hence, it may be envisaged to design the at least two guiding elements in such a way that the protrusions that are assigned to a guiding element involve tips which can just contact an opposite contact surface of a neighboring guiding element. Even when a minimum interference would be present in this case, this as such undesired connection could be separated as the guiding elements may be moved with respect to one another with little force.

In a finished state, i.e. when being used as a joint assembly, the guiding elements respectively have to provide only a defined range for the relative pivot movement. This may for instance involve a pivot range of ±60° about the X-axis and a pivot range of ±60° about the Y-axis. It is not necessary that the guiding elements, when in operation, have to be arranged to be arbitrarily rotated by large rotation angles or pivot angles with respect to one another. It is particularly not necessary that pivot angles of greater than 180° about the X-axis and/or the Y-axis have to be provided. In turn, this may be used to manufacture the at least two guiding elements in a first relative orientation with respect to one another and to transfer the at least two guiding elements by defined relative movement to a second operation orientation. In turn, this may be used to form elevations, nubs and such like at the contact surfaces that are only after a defined relative movement brought into an orientation that corresponds to their operation orientation (involving the pivot angles provided when in operation).

According to at least some embodiments, the guiding elements are not provided with ideally ball-shaped contact surfaces. Defined deviations from the ideal ball shape may be defined to simplify the generation of the elevations in the manufacturing orientation. In the operation orientation, the protrusions may be brought into a close contact with the opposite surfaces assigned thereto. In this way, the guiding clearance may overall be even further reduced.

A further measure for increasing the accuracy may involve a defined preloading to the outer guiding element that is applied from the exterior. In this way, the guiding elements may be at least sectionally deformed to fill gaps between the guiding elements that are caused by the manufacturing.

Overall, also with the additive manufacturing, a great guiding accuracy may be ensured. This enables the use of the joint assembly also in operation fields and/or in applications, wherein high precision and accuracy are of huge interest.

According to a further embodiment, the joint assembly comprises three guiding elements that form a central element, an intermediate element and an outer element that are concentrically arranged with respect to one another and integrally manufactured. In other words, the guiding elements are nested in one another, and, in some embodiments, loss-proof and/or undetachable.

Using three guiding elements that are arranged as a central element, an intermediate element and an outer element may have the effect that between the central element and the intermediate element, and between the intermediate element and the outer element, respectively, one of the above-mentioned pivot axes (X-axis, Y-axis) may be defined when the guiding elements are arranged to enable a respective pivot movement merely about this particular axis.

According to a refinement of the above embodiments, the outer element is arranged as a spherical shell, wherein the outer element undetachably surrounds the intermediate element, and wherein the intermediate element is arranged as a spherical shell and undetachably surrounds the central element.

According to a further embodiment, the central element comprises a central guide opening extending therethrough that is arranged for inserting an instrument shaft or a guiding shaft. In some embodiments, a longitudinal axis of the shaft of the inserted instrument intersects the center of the joint assembly, wherein also the pivot axes intersect. The point of intersection, which is in the center of the joint assembly, serves, so to say, as reference for enabled movements. In other words, the point of intersection may also be understood as zero point of the Cartesian coordinate system. It may be envisaged to integrally manufacture the central element and the guiding shaft. It may however also be envisaged to couple the central element with a guiding shaft that is separately manufactured.

According to a further embodiment of the joint assembly, the intermediate element and the outer element comprise groove-shaped guiding recesses, wherein at least one guiding recess of the intermediate element and at least one guiding recess of the outer element are angularly offset from one another and, in exemplary embodiments, oriented at an offset of 90° to one another. The groove-shaped guiding recesses may also be referred to as apertures in the shell-shape of the intermediate element and/or the outer element. In some embodiments, the guiding shaft and/or the inserted instrument extends through both the at least one guiding recess of the intermediate element and the at least one guiding recess of the outer element. In this way, the guiding shaft contributes to the definition of the relative positions between the guiding elements.

It is further preferred that the intermediate element and the outer element respectively comprise two guiding recesses which are formed at (radial) ends of the ball structure or spherical shell structure that are facing away from one another.

The guiding recesses of the intermediate element and the guiding recesses of the outer element jointly define a slotted guide for the guiding shaft and/or the shaft of the inserted instrument. Guiding recesses of the intermediate element define an enabled pivot range about the pivot axis to which the intermediate element is assigned. Guiding recesses of the outer element define an enabled pivot range and/or pivot angle about the pivot axis to which the outer element is assigned. Hence, the guiding recesses of the intermediate element and the outer element may jointly define the total enabled pivot range (for instance ±60° about the X-axis and ±60° about the Y-axis).

According to a refinement of the above-mentioned embodiment, the central element is provided with or arranged to be coupled to a guiding shaft that at least partially extends through the groove-shaped guiding recesses of the intermediate element and the outer element. The guiding shaft extends from a center of the central element radial to the exterior. The guiding shaft and the guiding opening of the central element are concentrically aligned to one another.

When the center of the joint assembly is regarded as a reference for the Cartesian coordinate system (X-Y-Z), the longitudinal extension of the guiding shaft and/or the guiding recess defined, at least in a neutral position, the Z-axis. The guiding opening also extends through the guiding shaft.

According to a further embodiment of the joint assembly, further at least one groove-shaped passage for a transmission shaft is formed at the outer element, wherein the passage is arranged to be coupled with the intermediate element, wherein the guiding recess of the outer element and the passage are angularly offset from one another and, in exemplary embodiments, offset from one another by 90°. The passage in the outer element ensures the accessibility of the intermediate element for a pivot axis for mounting the intermediate element.

For providing a defined pivot angle and/or pivot range in accordance with at least some embodiments, both the outer element and the intermediate element are arranged to be pivotably mounted to a base frame. Hence, both the outer element and the intermediate element may not be arbitrarily pivoted with respect to the base frame with respect to one another. Rather, for instance the intermediate element is mounted to the base frame in such a way that merely a pivot movement of the intermediate element about the X-axis is enabled. Accordingly, for instance, the outer element is mounted to the base frame in such a way that merely a pivot movement about the Y-axis is enabled. The guiding recesses of the outer element and the intermediate element intersect one another and jointly define a slotted guide opening through which the guiding shaft and/or the shaft of the instrument may be inserted in the central element or may be coupled thereto. In other words, the central element as such, which may be for instance ball-shaped, is basically freely mounted in the intermediate element and, eventually, also (mediately) freely mounted in the outer element, however the swivel orientation of the central element is defined by the guiding shaft and/or the shaft of the instrument that extends through the guiding recesses of the intermediate element and the outer element.

According to a further embodiment of the joint assembly, the at least two guiding elements are arranged as disposable parts. In some embodiments, in accordance with this embodiment, the central element, the intermediate element and the outer element are arranged as integrally manufactured disposable parts. The manufacturing simplifications elucidated in the context of this disclosure are eventually reflected in a significantly reduced manufacturing effort and material effort. This enables the configuration as disposable parts. In this way, the joint assembly is easily suitable for hygienically challenging applications, for instance in the medical-surgical field. By way of example, in accordance with this embodiment, no suitability for autoclaving has to be provided. A potentially soiled or contaminated joint assembly may easily be replaced. Hence, in spite of the configuration as a disposable part, overall the system costs for the guiding device, based on a single specific application, may be reduced in doing so.

According to a further embodiment, both at the intermediate element and at the outer element, at least one mount for a bearing flange is formed, respectively. The bearing flange is arranged to pivotably couple the intermediate element and/or the outer element to the base frame. It may however also be envisaged to form the pivot bearings for mounting the intermediate element and the outer element at least partially as integral components of the joint assembly. In some embodiments, the mounts of the outer element and the intermediate element are oriented perpendicular to one another.

In regard of the guiding device, the above and other objects of the present disclosure are achieved by a multi-axis-guiding device for an instrument, a medical instrument or a simulation instrument, for instance, wherein the guiding device comprises a base frame and a joint assembly in accordance with at least one of the afore-mentioned aspects that is mounted to the base frame, wherein the joint assembly provides two non-parallel pivot axes that intersect, in some embodiments, one another in a center of the joint assembly. For illustrative purposes, the pivot axes are designated by X and Y.

The non-parallel pivot axes may also be referred to as intersecting axes and further, however, as pivot axes that are arranged in a skewed fashion. The base frame may also be referred to as base housing or base structure.

According to an exemplary refined embodiment, the guiding device further comprises a first pivot actuator for the first pivot axis X that is coupled to the intermediate element of the joint assembly, and a second pivot actuator for the second pivot axis Y that is coupled to an outer element of the joint assembly, wherein the first pivot actuator is coupled to the intermediate element via the transmission shaft that extends through the outer element. It should be noted that the arrangement might also be just the opposite.

In this way, a drive for each of the pivot axes X, Y is provided. The pivot actuators may for instance be arranged as force-feedback drives. In this way, when being used in a simulation system, defined resistances may be "simulated". The pivot actuators may however also be applied for the use as an assistance system for surgical and/or operative procedures. By appropriately controlling the pivot actuators, a defined force-based signal may be outputted to the operating surgeon directly via the instrument. In this way, for instance, an operation area (in the interior of a human or animal body) may be divided in enabled ranges and non-enabled ranges. In case the operating surgeon should mistakenly try to penetrate a non-enabled range with the instrument, it may be clearly signaled that a penetration of a non-enabled range is likely to happen by a respective feedback (increased resistance).

The pivot actuators may however also be arranged to control the instrument in a stand-along fashion. Applications may be seen, for instance, in the field of telemedicine, the (technical and medical) diagnosis, and also in the field of simulation (for technical and/or medical purposes).

In accordance with a further embodiment, it is further preferred that the pivot actuators are configured to mediately or directly detect an actual swivel position with respect to the pivot axis ((X or Y) associated thereto. In this way, a position monitoring may be provided. The position detection may be absolute and/or relative.

According to a further embodiment, the guiding device further comprises a guiding shaft that is coupled to a central element of the joint assembly and that forms a linear guide for the instrument. Accordingly, a translatory axis is provided for the instrument and/or the instrument shaft. The translatory axis may also be referred to as Z-axis. In some embodiments, also the Z-axis intersects the center of the joint assembly.

According to a further embodiment, the guiding shaft and the central element further define a rotation axis Z for the instrument. Accordingly, the instrument may be rotated about the Z-axis that is oriented concentrically with respect to the longitudinal axis of the instrument shaft. Overall, the guiding device may thus provide four axes and/or four degrees of freedom of movement for the instrument.

According to a refinement of the above embodiment, the guiding device further comprises a translational actuator that is assigned to the guiding shaft and that is configured to engage the instrument shaft that is inserted in the guiding shaft for translational force transmission. To this end, the translational actuator may be provided with a gearwheel that cooperates with a linearly extending toothing of the instrument shaft. In other words, the instrument shaft may be at least sectionally arranged as a toothed rod.

The translational actuator may also be arranged as force-feedback actuator. The translational actuator may further be arranged so that and/or may be controlled in such a way that the instrument may be linearly moved along the Z-direction automatically by the translational actuator.

According to a further embodiment, the guiding device further comprises a rotation actuator that is assigned to the guiding shaft and that is configured to directly or mediately engage the instrument shaft that is inserted in the guiding shaft, for rotatory force transmission. In this way, also the rotation movement about the Z-axis may involve a force-feedback feature. The rotation actuator may further be arranged to automatically rotate the instrument shaft.

In accordance with a refinement of this embodiment, the rotation actuator mediately acts on the instrument shaft via the guiding shaft. That is, in other words, the rotation actuator may for instance involve a pinion that is coupled with a gear wheel that is arranged at the guiding shaft. The pinion may rotate the gear wheel about the Z-axis. In exemplary embodiments, when the instrument shaft is arranged in the guiding shaft in a rotation-proof fashion, the rotation about the Z-axis may be induced directly. Other arrangements may be envisaged.

According to a further embodiment of the guiding device, the guiding shaft is coupled to the base frame via a guiding unit, wherein the guiding unit is coupled to a rotation prevention feature. In exemplary embodiments, this involves a guiding chain that forms a hinged connection within the base frame and the guiding unit. In some embodiments, the guiding device is arranged at an end of guiding shaft that is facing away from the center of the joint assembly. As already described herein before, in some embodiments, the guiding shaft is rotatable about the Z-axis to provide a rotation axis for the instrument shaft. At the end of the guiding shaft that is facing away from the guiding unit, however, the central element of the joint assembly is formed. It is insofar beneficial to arrange the guiding unit at the end that is turned away.

In some embodiments, an arrangement is provided wherein the guiding unit assumes a defined rotation position (with respect to the Z-axis) as the guiding unit acts also a rotation reference for the (rotatable) guiding shaft. This, however, requires that the guiding shaft is arranged to be defined rotated about the X-axis and/or the Y-axis. In some embodiments, the rotation prevention feature is configured to sufficiently accurately locate the rotation position of the guiding unit (with respect to the Z-axis), however, to enable the joint swiveling of the guiding unit and the guiding shaft about the X-axis and/or about the Y-axis. This may be provided by a guiding unit arranged as a guiding chain that is, in some embodiments, hingedly mounted to the base frame and the guiding unit.

A further feature of the guiding chain involves that the guiding chain may also be used as drag chain (cable drag). Generally, a drag chain comprises a plurality of rigid chain links that are connected to one another by bolts that are parallel to one another, wherein the links are box-shaped and provide an intermediate space through which for instance cables and such like may be led. Generally, drag chains are bend-proof (against lateral bending due to a force application parallel to the chain bolts). Accordingly, a guiding chain that is arranged according to the drag chain type is suited to act as rotation prevention feature.

The guiding chain is, however, in some embodiments, arranged to tolerate, due to a compensation movement, pivot movements of the joint assembly about the X-axis and about the Y-axis that would have an effect on the orientation of the guiding shaft and the guiding unit. For instance, the guiding chain is coupled via a rotatably mounted to the guiding unit and, at the end thereof, that is facing away from the guiding chain via a rotatably mounted connector to the base frame. The rotatability of the connectors is in one exemplary embodiment to be interpreted as rotatability and/or pivotability about an axis that is perpendicular to the (parallel) bolt axes.

In some embodiments, the rotation actuator is mounted to the guiding unit and, thus, coupled via the rotation prevention feature to the base frame. In this way, the rotation actuator may for instance act via a pinion on a gear wheel that is arranged at the guiding shaft to be able to rotate together with the guiding shaft relative to the rotation actuator.

According to a further embodiment, a cable passage is formed between the guiding unit and the guiding shaft, wherein the cable passage comprises a slip ring contact to provide a cable guiding from the base frame via the guiding chain and the guiding unit to the guiding shaft, for instance to the translational actuator of the guiding shaft. According to at least some embodiments, the guiding shaft and the translational actuator mounted thereon are mounted rotatably about the Z-axis. This also involves a relative rotation with respect to the guiding unit (that is secured against rotation). The rotation passage insofar enables a signal transmission and/or energy transmission for any rotation angle.

According to a further embodiment, the guiding device further comprises a sensor unit that is assigned to the guiding shaft, wherein the sensor unit is configured to detect a translational movement and a rotation movement of the inserted instrument. In some embodiments, the sensor unit is mounted to the guiding unit and thus coupled to the base frame in a manner secured against rotation so that the guiding shaft and the instrument inserted therein may be rotated with respect to the sensor unit. In some embodiments, the sensor unit comprises a multi-dimensionally operative sensor or two sensors that are coupled to one another and that are jointly configured for detecting the translational movement and the rotation movement.

In other words, the sensor unit is arranged to detect rotations about the Z-axis and sliding movements along the Z-axis. The sensor unit monitors the movement of the instrument shaft. The sensor unit may also be referred to as 2D-sensor. The rotation and the sliding movement may be mediately or directly detected. Several measurement principles may be envisaged, for instance optical sensors, laser sensors, inductive sensors, capacitive sensors, and such like. Further, the sensor unit may basically involve sensors that are configured to measure absolute values, however, in the alternative or in addition, also sensors that are arranged to measure relative values.

In some embodiments, the guiding device overall comprises a sensor device to which the sensor unit is assigned, wherein the sensor device is configured to detect pivot movements about the X-axis, pivot movements about the Y-axis, translational movements along the Z-axis and rotation movements about the Z-axis. In this way, the movement of the instrument, particularly of the instrument shaft, may be completely monitored. Accordingly, an actual position of a tip of the instrument may be determined. In this way, in some embodiments, the guiding device is also arranged for position monitoring and/or for position detection. This may be used in a medical-operative operation mode as in this way complex optical and/or radiological procedures for determining the position and/or orientation of the instrument may be dispensed with. The position determination and/or position monitoring capability may also involve, in some embodiments, benefits and/or a simplified design for simulation systems as the effort for additional sensors may be avoided.

In regard of the method, the above and other objects of the present disclosure are achieved by a method for manufacturing a joint assembly for a multi-axis guiding device for an instrument, wherein the method involves the following steps:

additive manufacturing a plurality of at least sectionally ball-shaped guiding elements having spherical contact areas for forming a combined spherical bearing.

wherein at least two of the guiding elements are integrally manufactured in a concentric alignment, and wherein the at least two guiding elements enable a relative pivot movement.

In some embodiments, the method further involves a generation of at least one contact surface that is provided with a plurality of protrusions, for example a nubby contact surface in the contact areas. In some embodiments, the method is an additive method, for instance a 3D-printing procedure, stereolithographic procedure, laser sinter procedure, laser-melting procedure, and such like. In some embodiments, the method may performed without or with only a little need for finishing processing.

In some embodiments, the method is suited for forming a joint assembly according to at least one of the aforementioned aspects. It is noted that the method may be further refined in accordance with at least one of the aspects described herein which elucidate embodiments of the joint assembly.

In a further refinement, the method further involves:

additive, integrally manufacturing a central element, an intermediate element and an outer element, that form three guiding elements that are arranged concentrically to one another, wherein the outer element is arranged as a spherical shell and undetachably surrounds the intermediate element, wherein the intermediate element is arranged as a spherical shell and undetachably surrounds the central element, and wherein the central element comprises a central guide opening extending therethrough that is arranged for an insertion of an instrument shaft or a guiding shaft.

By way of example, the method further involves forming groove-shaped guiding recesses at the intermediate element and the outer element which assume a first relative orientation during the additive manufacturing, wherein a relative movement between the intermediate element and the outer element takes place after the additive manufacturing to define a second relative orientation between the groove-shaped guiding recesses that corresponds to a relative orientation in an operative state. In other words, the transfer of the guiding elements from the manufacturing orientation to the operation orientation may involve a defined relative pivot movement.

In regard of the use, the above and other objects of the present disclosure are achieved by a use of a joint assembly which is arranged in accordance with one of the afore-mentioned aspects and/or which is manufactured in accordance with one of the afore-mentioned method aspects as a spherical bearing for an instrument holder, such as an instrument holder for a simulation system or an assistance system for minimally invasive procedures, for instance. Minimally invasive procedures involve minimally invasive surgery and minimally invasive diagnosis. It should be noted that also other applications may be envisaged, for instance the use of the joint assembly in a guiding device for technical diagnosis or inspection. Further, the use for (technical) simulation systems may be envisaged. Generally, the joint assembly is suitable for a cost-efficient implementation of a multi-axial spherical bearing involving defined pivot angles for an instrument having a rod-shaped instrument shaft that comprises two, and, in some embodiments, three or four degrees of freedom.

The use of the instrument holder for an assistance system for minimally invasive procedures involves, in some embodiments, minimally invasive procedures at the human or animal body.

It is to be understood that the previously mentioned features and the features mentioned in the following may not only be used in a certain combination, but also in other combinations or as isolated features without leaving the spirit and scope of the present disclosure.

BRIEF DESCRIPTION OF THE DRAWINGS

Further features and advantages of the disclosure are disclosed by the following description of a plurality of exemplary embodiments, with reference to the drawings, wherein:

FIG. 7 is a perspective partial view of a joint assembly that is arranged to be used at the arrangement according to FIG. 1;

FIG. 8 is a view of the arrangement according to FIG. 7, wherein for illustrative purposes an outer element of the joint assembly is omitted;

FIG. 9 is a simplified exploded view of the embodiment according to FIGS. 7 and 8, wherein an intermediate element and an outer element are shown in a cross-sectional view;

FIG. 13 is a rear perspective partial view of the arrangement according to FIG. 1 for illustrating a translational drive;

FIG. 14 is a partial view of the arrangement according to FIG. 13 in an orientation that deviates from the orientation of FIG. 13;

FIG. 19 is a schematic partial view of an embodiment of an instrument holder that is provided with a guiding device, wherein the arrangement of FIG. 19 deviates from the arrangement according to FIG. 1;

FIG. 20 is a schematic, greatly simplified partial cross-sectional view of a joint assembly for illustrating contact areas between guiding elements.

DETAILED DESCRIPTION OF EXEMPLARY EMBODIMENTS

Figure 1:
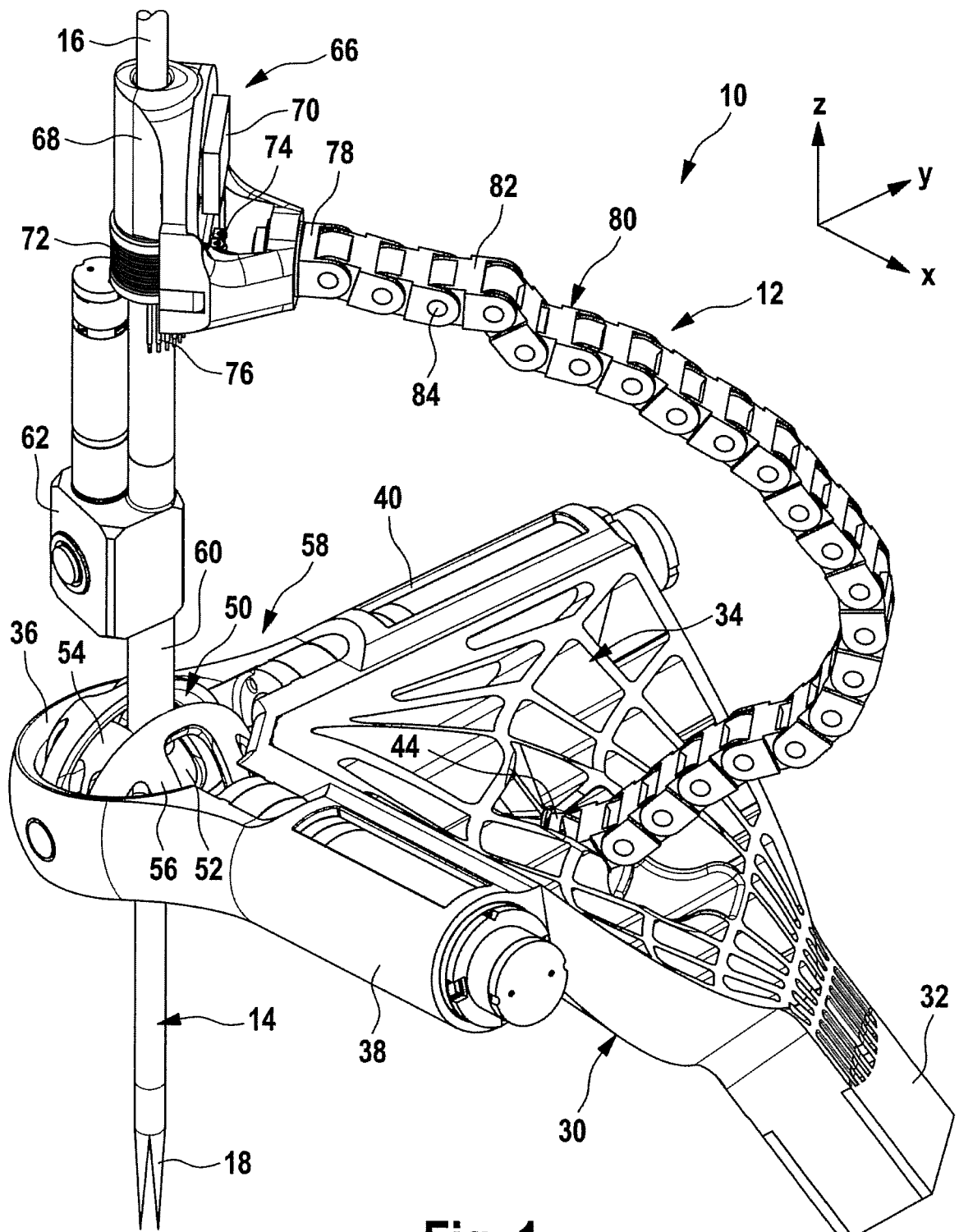
FIG. 1 is a perspective view of an instrument holder that is provided with a guiding device to which an instrument is mounted.

FIG. 1 shows a perspective view of an instrument holder that is designated by 10. The instrument holder 10 comprises a guiding device 12 that is arranged as a multi-axis guiding device. An instrument 14 is mounted to the guiding device 12. By way of example, the instrument 14 may be arranged as an instrument for minimally invasive surgery or a simulation instrument for minimally invasive surgery. The instrument 14 may further be arranged as a diagnostic instrument, an inspection instrument, and a simulation instrument for technical applications, for instance for parts inspection, error diagnosis and such like.

The instrument 14 comprises a shaft 16 that is rod-shaped and that comprises a longitudinal extension that is significantly greater than the cross-sectional extension. The instrument 14 is mounted via the shaft 16 to the guiding device 12. The shaft 16 generally comprises a distal and a proximal end. In FIG. 1, a tool 18 is arranged at the distal end of the shaft 16, for instance a tool for minimally invasive surgery. At least in accordance with some embodiments, at the proximal end of the shaft 16, a handle 20 is arranged, confer particularly FIG. 19. The tool 18 can be controlled by the handle 20. Further, the position and/or orientation of the entire instrument 14 may be altered to achieve a target position with the tool 18. The positioning is performed in a defined fashion as the instrument 14 is mounted to the guiding device 12 in a movably guided fashion.

For illustrative purposes, in at least some of the figures described herein further below a (Cartesian) coordinate system X-Y-Z is shown which shall be used hereinafter for elucidating defined directions and orientations. It goes without saying that the coordinate system X-Y-Z merely serves for illustrative and elucidative purposes, and not to limit the scope of the disclosure. It should be further noted that also different coordinate systems involving different orientations and associations may be used for describing the several embodiments and aspects of this disclosure. It is within the discretion of the skilled person to apply respective (conceptual) transformations.

The same applies hereinafter to direction indications and to indications for a spatial classification, such as for top, bottom, lateral, frontal, rear, and such like. In addition, the use of these terms shall not be interpreted in a limiting sense. When these terms are used in a context of defined illustrations and orientations, they relate to the actually shown illustration and may thus be replaced in modified illustrations that are associated with modified orientations and view directions by respectively modified allocation terms.

Figure 2:
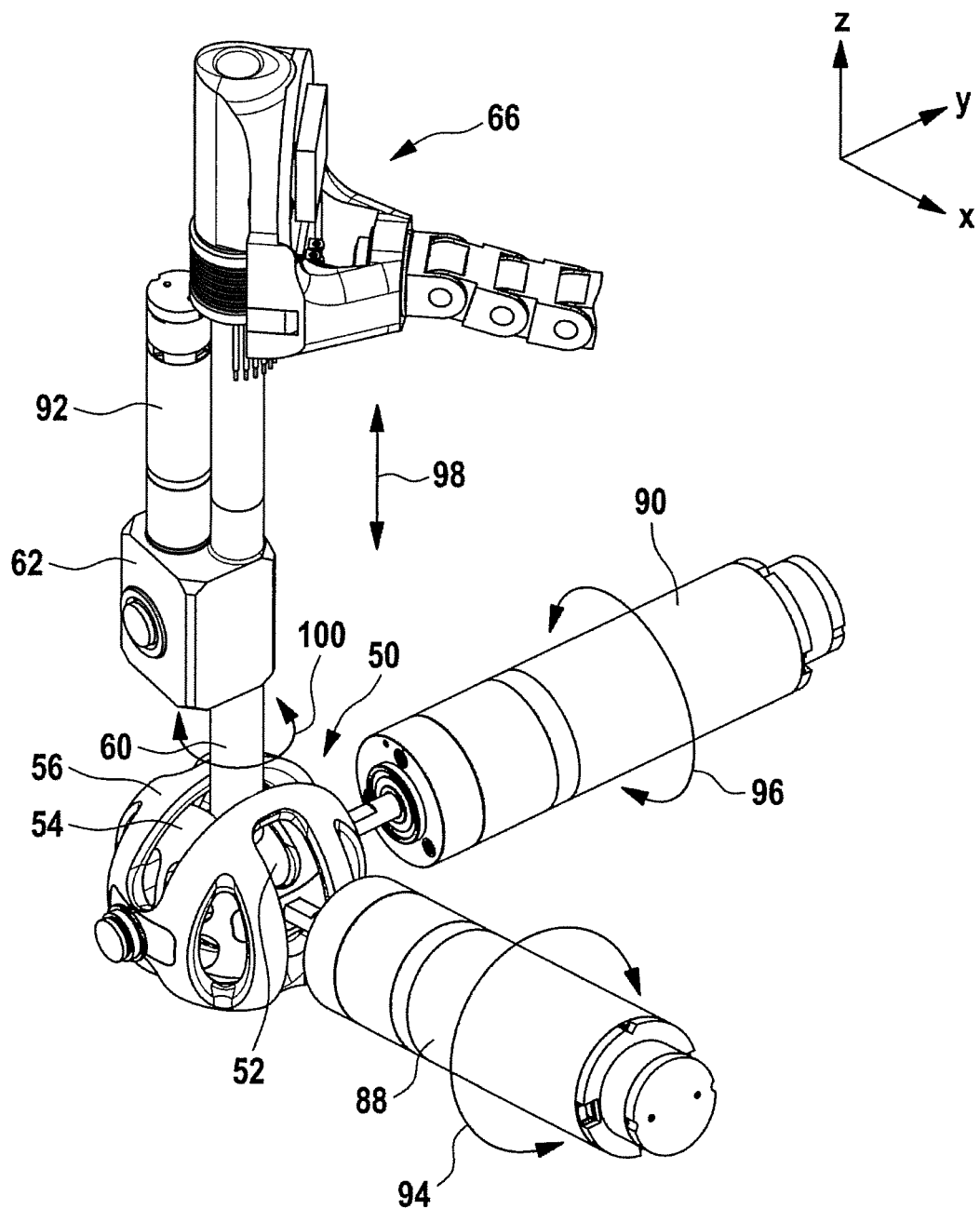
FIG. 2 is a further view of the guiding device according to FIG. 1 in an orientation that corresponds to the view of FIG. 1, wherein for illustrative purposes components are omitted.

At least in a neutral position, the shaft 16 of the instrument 14 is parallel to the Z-axis. The guiding device 12 elucidated with reference to FIG. 1 is arranged as a multi-axis guiding device, for instance as a 4-axes guiding device. In other words, the guiding device 12 comprises in total four degrees of freedom for the instrument 14. Those degrees of freedom involve pivot movements about the X-axis and about the Y-axis, a translational movement along the Z-axis (and/or contrary to the Z-axis) and a rotation about the Z-axis. For instance, those movement directions are indicated in FIG. 2 by double arrows 94, 96, 98, 100 to which additional reference is made. The double arrow 94 elucidates a pivot movement about the X-axis. The double arrow 96 elucidates a pivot movement about the Y-axis. The double arrow 98 elucidates a translational sliding movement along the Z-axis. The double arrow 100 elucidates a rotation movement about the Z-axis.

The guiding device 12 of the instrument holder 10 is arranged to provide the desired degrees of freedom of movement for the instrument 14. The guiding device 12 comprises a base frame 30 which may also be referred to as housing or rack. The base frame 30 comprises in a rear region a connector 32 which may also be referred to as adapter piece or connector flange. Vie the connector 32, the guiding device 12 may be fixedly mounted, for instance to an operation table or to an apparatus for simulating medical procedures. In case of an application in the technical field, for instance for inspection purposes or diagnostic purposes, the base frame 30 may be mounted to a tool table or such like via the connector 32.

The base frame 30 comprises a central portion 34 that adjoins the connector 32. The central portion 34 comprises, for instance, a stiffening ribbing. At the end of the central portion 34 that is facing away from the connector 32, the base frame 30 comprises a pivot bearing 36 that may also be referred to as seat. The base frame 30 further comprises a first drive mount 38 and a second drive mount 40 that are arranged in the vicinity of the pivot bearing 36 and the central portion 34. In other words, the first drive mount 38 and the second drive mount 40 form flanks of base frame 30 that lead into the pivot bearing 36. In some embodiments, the first drive mount 38 is oriented approximately perpendicular to the second drive mount 40. Extending from the connector 32, the base frame 30 is formed similar to a cantilever or a pent roof. In the central portion 34 approximately in the center, a bearing part 44 is arranged by which the base frame 30 may be coupled to a guiding chain 80 in a hinged fashion.

According to at least some embodiments, the base frame 30 is integrally manufactured as one piece. By way of example, an injection molding process may be used to this end. In some embodiments, a considerable ribbing in the central portion 34 ensures nevertheless a great stiffness and a sufficiently huge deformation resistance. In some embodiments, when only a little lot size of the base frame 30 is to be manufactured, also additive manufacturing processes may be used for producing the base frame.

At the ball socket shaped pivot bearing 36 of the base frame 30, a joint assembly 50 is received in a defined rotatable fashion. For illustrating an exemplary embodiment of the joint assembly 50, reference is made again to FIG. 1 and in addition to FIG. 2. In FIG. 2, for illustrative purposes, the base frame 30 of the guiding device 12 is omitted.

The joint assembly 50 is formed as a spherical joint assembly. The joint assembly 50 comprises three guiding elements that are nested in one another and concentrically arranged with respect to one another. In the center of the joint assembly 50, a central element 52 is arranged which is ball-shaped. The guiding elements may also be referred to as ball elements or spherical elements. The central element 52 is surrounded by an intermediate element 54 that is arranged as a spherical shell. The intermediate element 54 is surrounded by an outer element 56 that is arranged as a spherical shell. The central element 52, the intermediate element 54 and the outer element 56 form together a spherical bearing 58. The spherical bearing 58 provides in an exemplary embodiment a gimbal bearing of the instruments 14 at the guiding device 12.

Figure 3:
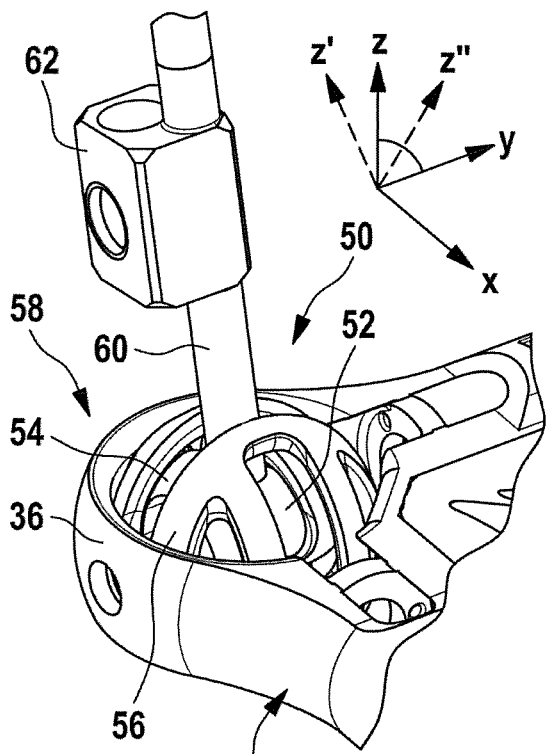
FIGS. 3 to 6 show partial views of the arrangement of FIG. 1 in the region of a joint assembly, wherein FIG. 3 and FIG. 4 elucidate angular positions with respect to a pivot axis (Y-axis) and wherein FIG. 5 and FIG. 6 elucidate angular positions with respect to another pivot axis (X-axis)
Figure 4:
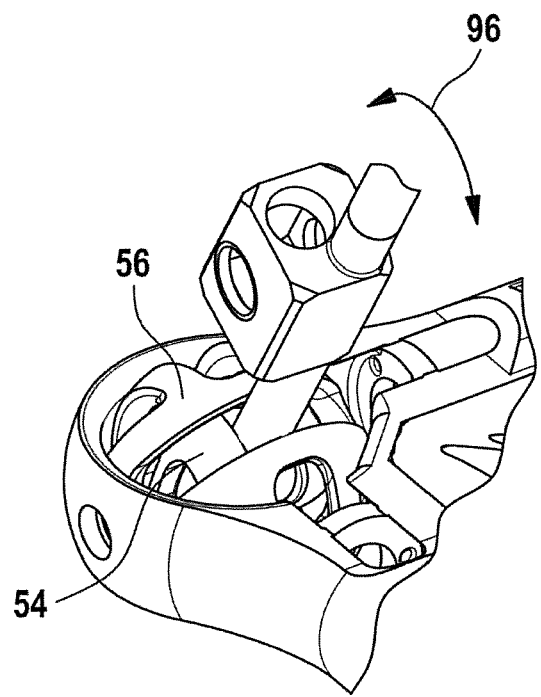
Figure 5:
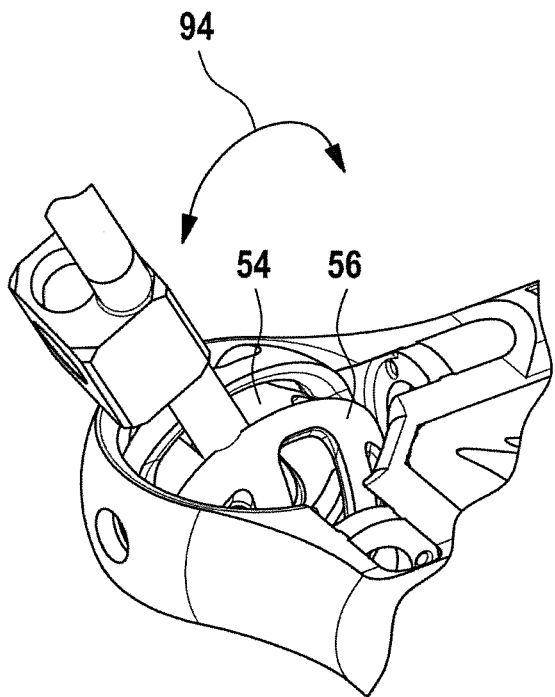
Figure 6:
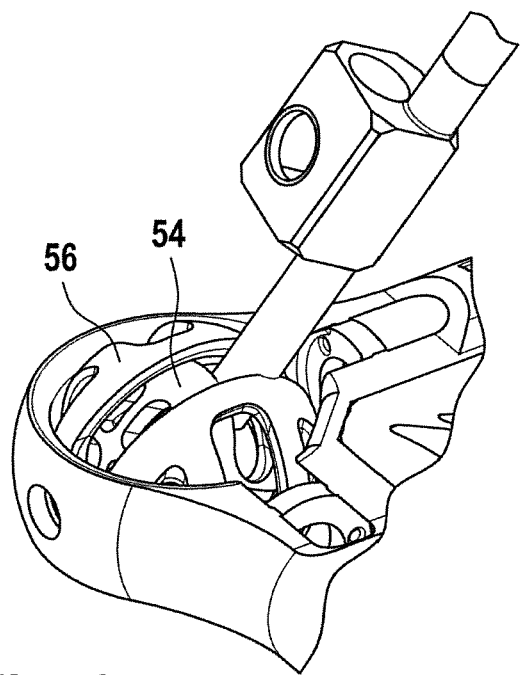

For elucidating the degrees of freedom of movement that are provided by the spherical bearing 58, additional reference is made to the FIGS. 3 to 6. FIG. 3 and FIG. 4 illustrate a pivot movement about the Y-axis; refer to the double arrow 96. FIG. 5 and FIG. 6 illustrate a pivot movement about the X-axis; refer to the double arrow 94. It should be noted that the spherical bearing 58 enables also intermediate positions, i.e. also simultaneous displacements about the X-axis and about the Y-axis. Detail views of the joint assembly 50 that forms the spherical bearing 58 are provided in FIGS. 7, 8 and 9, which will be addressed further below. In FIG. 3, axis directions are indicated by Z' and Z" to illustrate that the pivot movement may involve a displacement from an ideal orientation of the Z-axis.

Reference is made again to FIG. 1 and FIG. 2. Further, a guiding shaft 60 is assigned to the joint assembly 50. The guiding shaft 60 is mounted to the central element, refer also to FIG. 9. The guiding shaft 60 surrounds the shaft 16 of the instrument 14, at least sectionally. The guiding shaft 60 defines an actual orientation of the instrument 16. A zero point of the coordinate system X-Y-Z is, for instance, positioned in the center of the joint assembly 50. If this as the case, then the Z-axis would be pivoted with respect to the X-axis and/or the Y-axis, i.e. assuming a displaced position, starting from its perpendicular orientation, when the shaft 60 and the central element 52 coupled thereto are pivoted about the center of the joint assembly 50. For the sake of simplicity, it will be assumed hereinafter that the shaft 60 and the central element 52 define an (actual) Z-axis for the instrument 14. Further, a third drive mount 62 that accommodates a translatory drive is arranged at the guiding shaft 60.

At the proximal end of the guiding shaft 60, a guiding unit 66 is arranged that comprises a sensor housing 68 that accommodates a sensor unit 70. The sensor housing 68 is formed as an extension of the guiding shaft 60. Between the sensor housing 68 and the guiding shaft 60 there is further provided an annular contact 72 that is associated with a rotary union for cables. The guiding shaft 60 is rotatable about its longitudinal axis (Z-axis). A rotation prevention feature prevents such a rotation about the Z-axis of the guiding unit 66. Accordingly, a relative rotation between the guiding unit 66 and the guiding shaft 60 may take place. For transmitting signals and energy from a connector 74 that is assigned to the guiding unit 66 two conductors 76 that are assigned to the guiding shaft 60, a rotary passage including the annular contact 72 is provided which may be contacted, for instance, by sliding contacts.

At the sensor housing 68 of the guiding unit 66, further a bearing part 78 is arranged which is configured to be connected to the guiding chain 80. The guiding chain 80 thus extends between the bearing part 44 at the base frame 30 and the bearing part 78 at the sensor housing 68. The guiding chain 80 involves a plurality of chain links 82 that are connected to one another by bolts 84. In some embodiments, the guiding chain 80 is formed similar to a drag chain and provides a passage for cable routing. In other words, the guiding chain 80 may accommodate a wiring harness that contacts the contact 74. The guiding chain 80 is, in some embodiments, arranged as bend resistant chain and provides a great resistance moment against laterally applied forces that are oriented parallel to the bolts 84. In other words, the guiding chain 80 is, in some embodiments, sufficiently stiff so that the bolts 84 maintain their parallel orientation with respect to one another. It is ensured in this way that the guiding unit 66 undergoes only a little or no relative rotation about the Z-axis, when the instrument 14 is moved in the guiding device 12. The guiding chain 80 which is hingedly mounted to the base frame 30 and to the guiding unit 66 via the bearing parts 78, 44 enables a desired pivotability of the guiding unit 12 about the X-axis and/or about the Y-axis, together with the guiding shaft 60.

The sensor unit 70 that is accommodated in the sensor housing 68 is, in some embodiments, arranged as a sensor unit that is effective in two dimensions. In other words, the sensor unit 70 is configured to detect a translational movement of the instrument 14 along the (instantaneous Z-axis and a rotation of the instrument 14 about the (instantaneous Z-axis, wherein the rotation, in accordance with the exemplary embodiment illustrated herein, takes place as a joint rotation of the guiding shaft 60 and the instrument 14. In other words, the instrument 14 is mounted to the guiding shaft 60 in a fashion locked against rotation but arranged to be moved translatory along the Z-axis in the guiding shaft 60. A rotation reference is provided by the guiding chain 80, as the guiding unit 66 may not be rotated about the Z-axis.

By way of example, the sensor unit 70 comprises two sensors one of which detects the translational movement and the other one detects the rotation movement of the shaft 16 of the instrument 14. It may be however also envisaged to provide a 2D-sensor, for instance a 2D-laser sensor that probes a surface of the shaft 16 to detect translational movements and rotation movements.

It can be seen in FIG. 2 that the guiding device 12 illustrated therein comprises a first drive 88, a second drive 90 and a third drive 92. The first drive 88 is assigned to the X-axis. The second drive 90 is assigned to the Y-axis. The third drive 92 is assigned to the Z-axis. The drives 88, 90 are arranged as pivot drives; confer the double arrows 94, 96 that indicate pivot movements about the X-axis and/or about the Y-axis. The third drive 92 is arranged as a translational drive, confer the double arrow 100 that illustrates a sliding movement along the Z-axis. In accordance with the exemplary embodiment that is illustrated with reference to FIGS. 1 and 2, the guiding device 12 does not comprise a separate drive for the rotation movement about the Z-axis, refer to the double arrow 100. However, further embodiments may be envisaged wherein a respective drive is provided, refer also to FIG. 19, which will be detailed further below.

The drives 88, 90, 92 of the guiding device 12 may be arranged, for instance, as so-called force-feedback drives. In this way, it is not the primary purpose of the drives 88, 90, 92 to actively move the instrument 14 that is mounted to the instrument holder 10, but to support the user when guiding the instrument 14. However, it may basically be envisaged for at least some embodiments that the instrument 14 is fully automated moved by the drives 88, 90, 92 without the need of a manual intervention.

It may be further envisaged to couple the drives 88, 90, 92 with respective sensors to detect an actual position and an actual orientation of the instrument 14 with respect to the X-axis, the Y-axis and the Z-axis. Hence, for instance the drives 88, 90 may be used to mediately determine the pivot position of the guiding shaft 60 that is coupled to the central element 52 through the actual pivot position of the intermediate element 54 and the outer element 56. Similarly, also the third drive 92 may be used to determine a longitudinal position of the instrument 14 along the Z-axis. However, when the guiding device 12 is provided with the sensor unit 70 that is arranged to detect the sliding position of the instruments 14, the third drive 92 does not necessarily have to be used for position determination. It goes without saying that in addition or in the alternative to the drives 88, 90, 92 separate sensors may be implemented which may be used for position determination, for instance rotation angle sensors that are coupled to the first drive 88 and/or the second drive 90. However, the rotation angle determination may also be performed mediately when for instance the first drive 88 and the second drive 90 are used as relative rotation angle transducers or absolute rotation angle transducers.

With reference to FIG. 7, FIG. 8 and FIG. 9, an exemplary embodiment of the joint assembly 50 will be elucidated in more detail. In some embodiments, the joint assembly 50 is integrally manufactured by means of additive manufacturing. In other words, the central element 52, the intermediate element 54 and the outer element 56 are jointly manufactured, wherein further the central element 52 is undetachably arranged in the intermediate element 54 and wherein the intermediate element 54 is undetachably arranged in the outer element 56. In other words, the central element 52, the intermediate element 54 and the outer element 56 may only be separated from one another, when at least two of those parts are destroyed.

It can be seen from the exploded view according to FIG. 9 that the guiding elements 52, 54, 56 are nested in one another. In some embodiments, a common center of the guiding elements 52, 54, 56 defines the point, wherein the pivot axes X, Y and the translatory axis and/or rotation axis Z intersect one another. In this way, the integrally manufactured unit that forms the guiding elements 52, 54, 56 may provide the function of a gimbal bearing which otherwise may only be achieved at huge manufacturing effort and assembly effort.

The central element 52, the intermediate element 54 and the outer element 56 are formed in such a way that between the single elements, respectively, only defined pivot movements are enabled. At the intermediate element 54 groove-shaped guiding recesses 104 are formed. At the outer element 56, groove-shaped guiding recesses 106 are formed. The guiding recesses 104, 106 are in one operation configuration of the joint assembly 50, oriented perpendicular to one another, refer also to FIG. 7. Further, at least one groove-shaped passage 108 is formed at the outer element 56, wherein the intermediate element 54 may be contacted by the first drive 88, refer in this context also to FIG. 2.

Accordingly, the intermediate element 54 and the outer element 56 are not arranged as continuous spherical shells but rather as partially open spherical shells. It may be appreciated to provide windows, recesses and such like at the intermediate element 54 and/or the outer element 56. In this way, material costs may be minimized. In some embodiments, functional benefits may be provided, for instance an improved snuggling of the (remaining) contact areas and/or a smooth movability. In FIG. 7, windows in the outer element 56 are designated by 116. In FIG. 8, apertures in the intermediate element 54 are designated by 114.

In accordance with the operation configuration of the joint assembly 50 shown in FIG. 7, the guiding shaft 60 extends through both a guiding recess 104 of the intermediate element 54 and a guiding recess 106 of the outer element 56.

At least one bearing flange 120 is mounted to or formed at the intermediate element 54. At least one bearing flange 122 is mounted to or formed at the outer element 56. In accordance with the embodiment elucidated with reference to FIGS. 7 to 9, the bearing flanges 120, 122, two of which are respectively provided, are formed as separate parts that are mounted to a base body of the intermediate element 54 and/or the outer element 56. Accordingly, the intermediate element 54 comprises at least one receptacle 124 for the at least one bearing flange 120. Further, the outer element 56 comprises at least one receptacle 126 for the at least one bearing flange 122, refer also to FIG. 9. The bearing flanges 120, 122 enable an areal force application to the intermediate element 54 and/or the outer element 56 and may thus significantly increase the load capacity of the joint assembly 50.

Further, a bearing shaft 130 and a transmission shaft 132 are mounted to the intermediate element 54. The bearing shaft 130 and the transmission shaft 132 jointly define the pivot axis for the intermediate element 54 (X-axis). The bearing shaft 130 and the transmission shaft 132 are mounted to the bearing flanges 120. The bearing shaft 130 is, in the assembled state, mounted to the base frame 30. The transmission shaft 132 is, in the assembled state, coupled to the first drive 88.

At the outer element 56, a bearing shaft 134 and a transmission shaft 136 are arranged that are coupled with the bearing flanges 122. In the mounted state, the bearing shaft 134 is mounted to the base frame 30. In the mounted state, the transmission shaft 136 is coupled to the second drive 90. The bearing shaft 134 and the transmission shaft 136 jointly define a pivot axis (Y-axis) for the outer element 56.

Accordingly, the intermediate element 54 and the outer element 56 provide overall two pivot axes (X-axis, Y-axis) for the guiding shaft 60 that is mounted and/or coupled to the central element 52. The guiding recesses 104, 106 define in this connection allowed pivot ranges for the guiding shaft 60.

The central element 52 is ball-shaped and mounted to the receptacle of the intermediate element 54 that forms a bearing seat. The central element 52 and the shaft 60 mounted thereto are generally freely rotatable about the longitudinal axis of the shaft 60 (Z-axis). Pivot movements about the X-axis and/or about the Y-axis are enabled only in an allowed range, due to the cooperation with the intermediate element 54 and the outer element 56.

At the central element 52, a spherical contact surface 140 is formed which cooperates with a spherical contact surface 142 at the intermediate element 54. The contact surface 140 is formed as a convex spherical contact surface. The contact surface 142 is formed as a concave spherical contact surface. At the intermediate element 54, an outer contact surface 144 is formed that cooperates with an inner contact surface 146 of the outer element 56. The contact surface 144 may also be referred to as convex spherical contact surface. The contact surface 146 may also be referred to as concave spherical contact surface. Further, at the outer element 56, an outer contact surface 148 is formed. The contact surface 148 may also be referred to as convex spherical contact surface. In the assembled state, refer to FIG. 1, the contact surface 148 contacts a contact surface 150 that is formed at the pivot bearing 36 of the base frame 30 for accommodating and guiding the joint assembly 50, confer also FIG. 10 and FIG. 11. The contact surface 150 may also be referred to as concave spherical contact surface or as contact bearing seat.

FIG. 9 further elucidates that at the central element 52 and/or at the guiding shaft 60 a guide opening 154 extending therethrough is formed that is aligned concentrically with respect to the Z-axis. In the mounted state, the shaft 16 of the instrument extends through the guide opening 154. In addition, the guide opening 154 and/or the longitudinal axis thereof intersects the center of the joint assembly 50.

Figure 10:
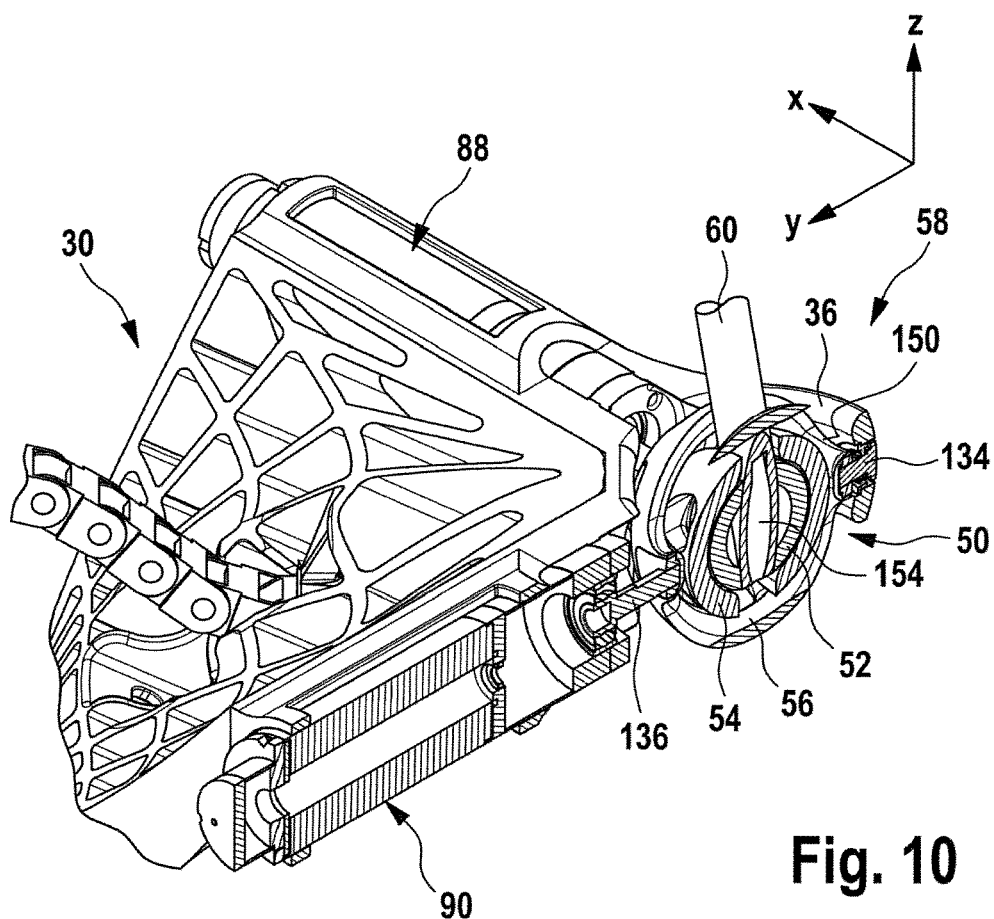
FIG. 10 is a perspective partial cross-sectional view of the arrangement according to FIG. 1 in a first orientation for illustrating a pivot drive.
Figure 11:
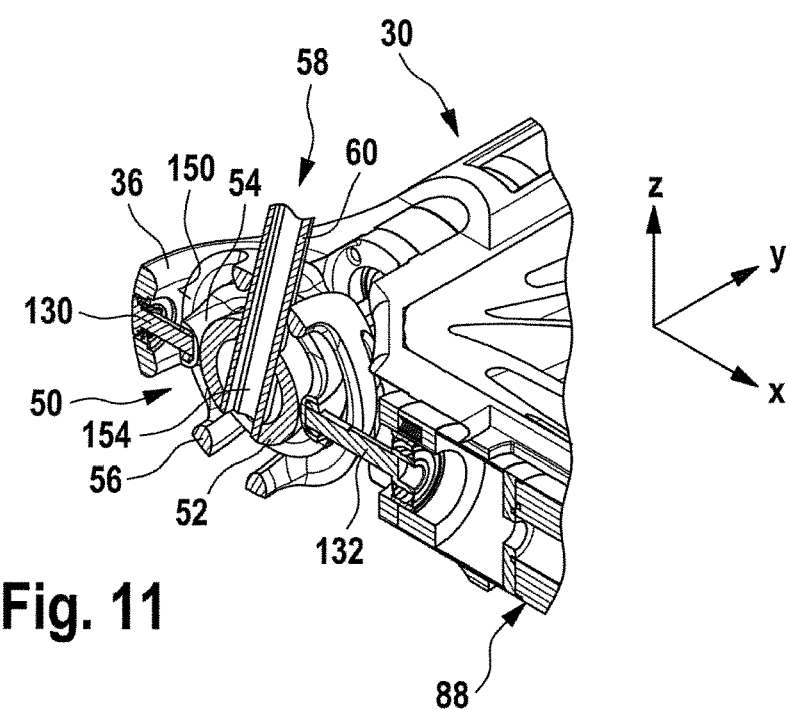
FIG. 11 is a further perspective partial cross-sectional view of the arrangement according to FIG. 10 in a deviating orientation for illustrating a further pivot drive.

FIG. 10 and FIG. 11 illustrate perspective Partial cross-sectional views of the guiding device 12, wherein the Sectional plane is respectively oriented perpendicular to the plane that is spanned by the X-axis and the Y-axis. FIG. 10 illustrates a cross-section through the second drive 90. FIG. 11 shows a cross-section through the first drive 88. The sectional plane in FIGS. 10 and 11 are oriented at an offset of 90° to one another. FIG. 10 elucidates that the outer element 56 of the joint assembly 50 is mounted to the base frame 30 via the bearing shaft 134. At the opposite side of the outer element 56, the joint assembly 50 is coupled to the second drive 90 via the transmission shaft 136. Similarly, FIG. 11 elucidates that the intermediate element 54 is mounted to the base frame 30 via the bearing shaft 130. At the opposite side of the intermediate element 54, the intermediate element 54 is coupled to the first drive 88 via the transmission shaft 132. The guide opening 154 forms a mount for the shaft 16 of the instrument 14 at the central element 52 and/or at the guiding shaft 60. The axes of the involved components intersect one another in the center of the concentric joint assembly 50.

Figure 12:
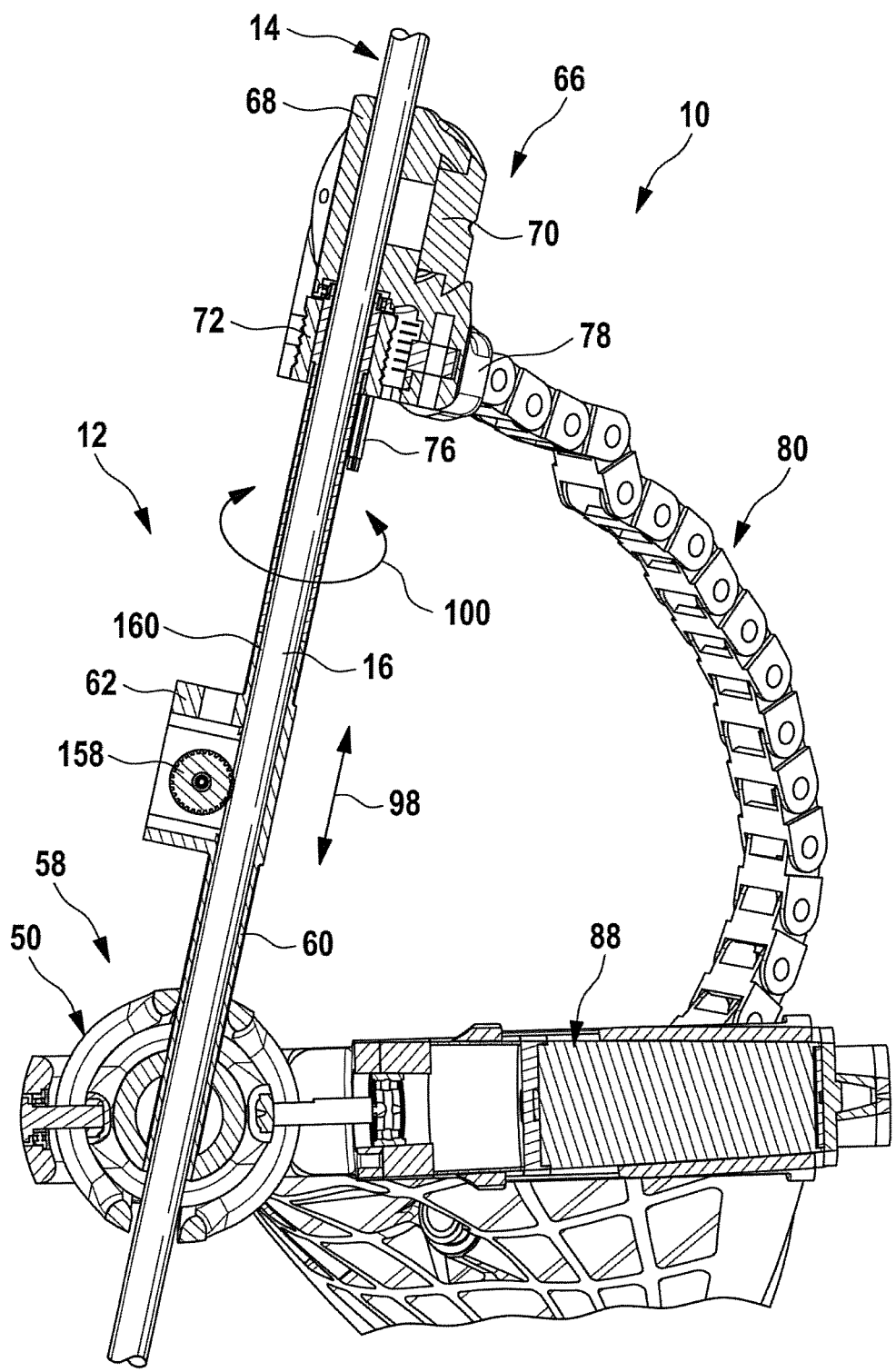
FIG. 12 is a further partial cross-sectional view of the arrangement according to FIG. 1.
Figure 15:
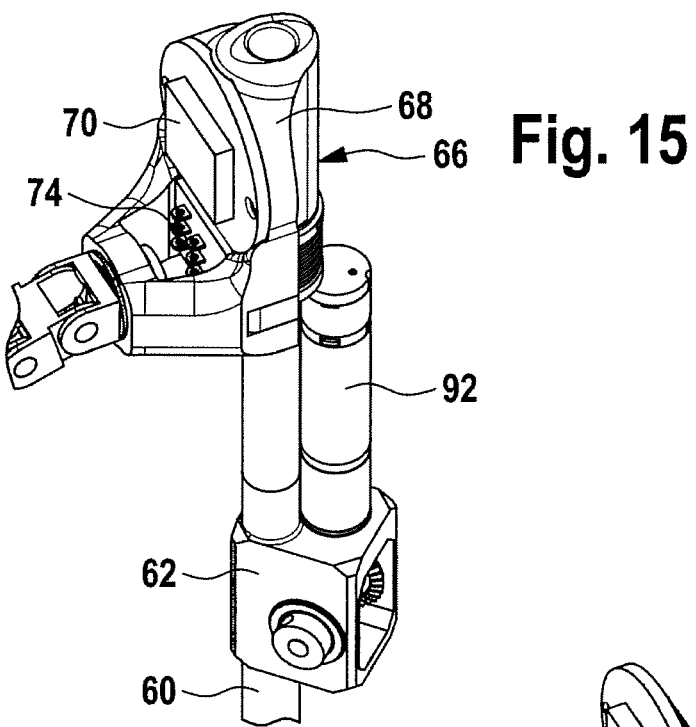
FIG. 15 is a view of the arrangement according to FIG. 14 in an orientation that deviates from the orientation of FIG. 14.

FIG. 12 elucidates a longitudinal cross-section through the guiding shaft 60, wherein the sectional plane is perpendicular to the longitudinal axis of a gear wheel 158 that is accommodated in a housing that is provided by the third drive mount 62. In other words, the gear wheel 158 is mounted to the guiding shaft 60 and coupled to the central element 52 of the joint assembly 50 via the guiding shaft 60. The gear wheel 158 engages a toothing 160 of the shaft 16 of the instrument 14, when the instrument is inserted in the guiding shaft 60. In other words, the shaft 16, at least in some exemplary embodiments, is sectionally arranged as a toothed rod and/or provided with a toothed rod toothing.

Additional reference is made to FIG. 13 that shows a rear view of the housing of the third drive mount 62. The gear wheel 158 is arranged at a drive shaft 164 that is perpendicular to the longitudinal extension of the guiding shaft 60. The drive shaft 164 is further coupled to the third drive 92 that is oriented perpendicular to the drive shaft 164. An output of the third drive 92 comprises a pinion 166 that is formed as a bevel gear. The pinion 166 engages a crown wheel 168 that is formed as a bevel gear. The pinion 166 and the crown wheel 168 jointly enable a 90°-redirecting of the drive movement of the third drive 92, so that the gear wheel 158 acts on the toothed rod 160 to slidingly move the instrument 14, refer to the double arrow 98 in FIG. 12.

The third drive 92 is oriented parallel to the longitudinal extension of the guiding shaft 60. In this way, the guiding device 12 is considerably compact shaped in the region of the guiding shaft 60. It should be noted that the translational drive for the instrument 14 may also be differently shaped.

Figure 16:
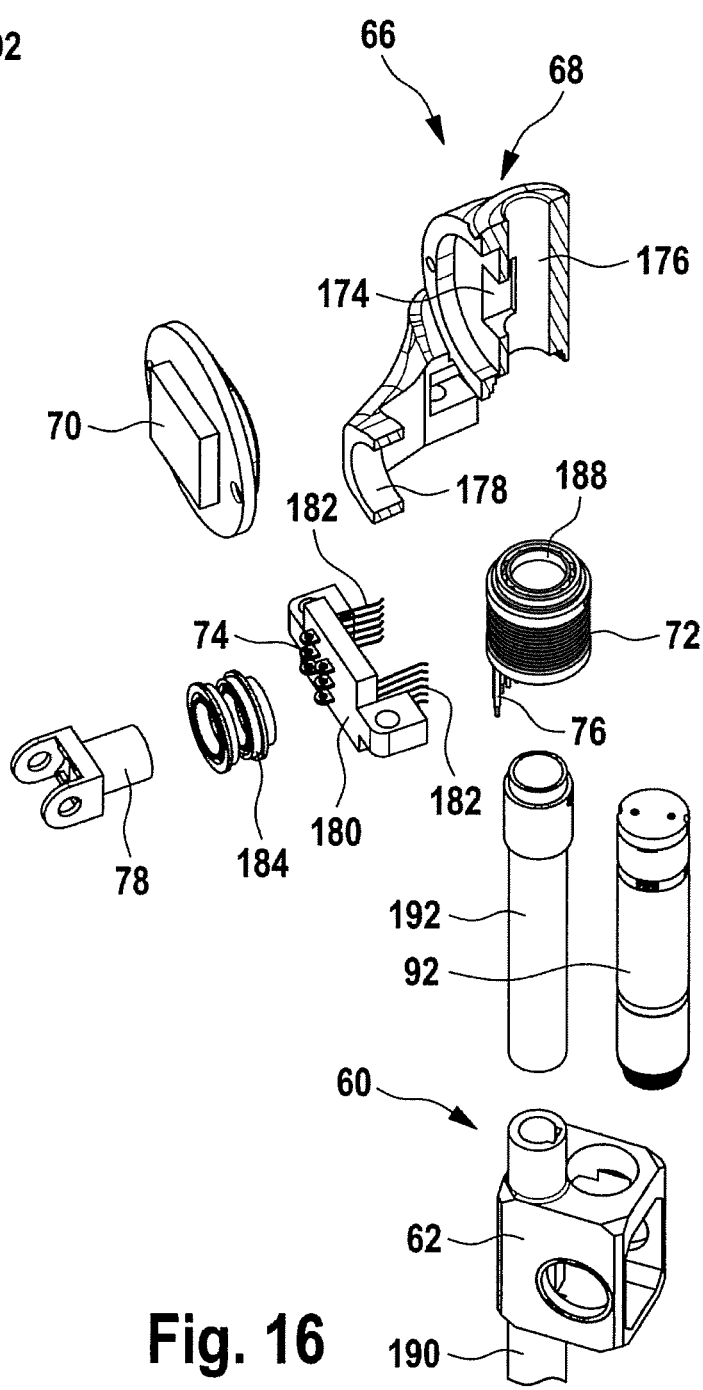
FIG. 16 is an exploded view of the arrangement according to FIG. 15, wherein a sensor housing is shown in a cross-sectional state.

Again referring to FIG. 12 and with additional reference to FIGS. 13 to 16, an embodiment of the guiding unit 66 is elucidated in more detail. A crossed-out arrow designated by 170 in FIG. 14 indicates that the guiding unit 66 is just not arranged to be pivoted about the Z-axis. This is provided by the guiding chain 80 that secures the guiding unit 66 at the base frame 30 against a rotation about the Z-axis. However, for supplying the third drive 92 with energy and with control signals, a rotary joint for the required supply lines is formed between the guiding unit 66 and the guiding shaft 60. FIG. 16 details in an exploded view the arrangement of the guiding unit 66 in an orientation in accordance with FIG. 15. The sensor housing 68 comprises a recess 174 for the sensor unit 70. The sensor unit 70 may detect the shaft 16 of the instrument 14 via the recess 174. The shaft 16 is arranged in a guide 176 of the sensor housings 68. Further, a bearing seat 178 is formed at the sensor housing 68 that is oriented basically perpendicular to the longitudinal extension of the guide 176. At the bearing seat 178, the bearing part 78 is hingedly mounted, using a bearing 184.

Further, a carrier 180 is coupled to the sensor housing 68 that supports connector contacts 74. Further, sliding contacts 182 are arranged at the carrier 180 that contact the annular contact 72 in the mounted state. The annular contact 72 may rotate with respect to the sliding contacts 182 without an interruption of the contact. Between the annular contact 72 and the sensor housing 68, a bearing 188 is formed that enables a relative rotation between the annular contact 72 (and/or the guiding shaft 60) and the sensor housing 68 of the guiding unit 66. The annular contact 72 is mounted to the guiding shaft 60 in a fashion secured against rotation. By way of example, the guiding shaft 60 is a multi-part component and provided with a bottom shaft part 190 and a top shaft part 192. The annular contact 72 is mounted to the top shaft part 192 in a fashion secured against rotation.

Figure 17:
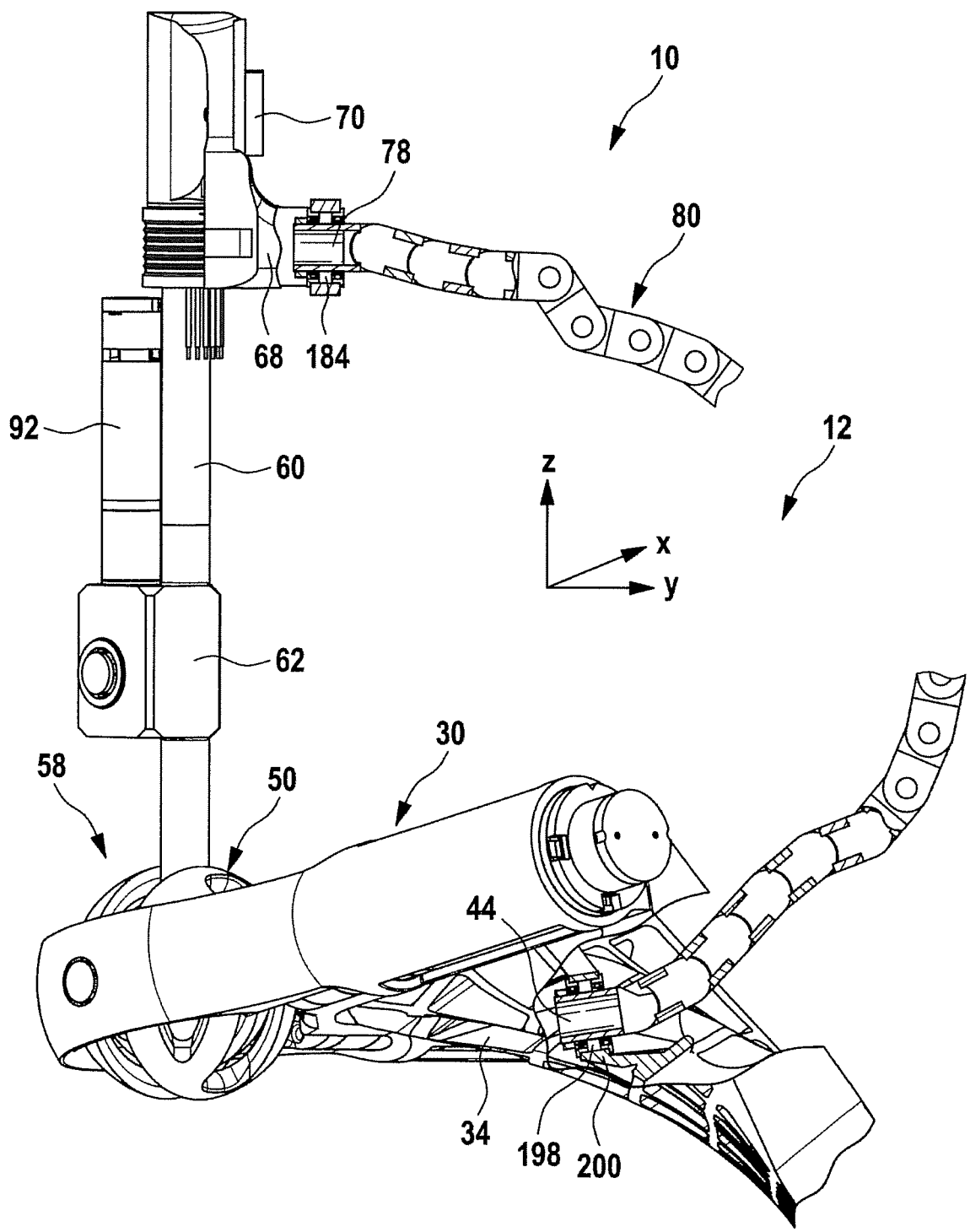
FIG. 17 is a partially cross-sectional partial view of an arrangement according to FIG. 1 for illustrating an arrangement of a guiding chain.

FIG. 17 illustrates a partially cross-sectional view of the instrument holder 10 according to FIG. 1, wherein the view plane is oriented parallel to the plane in which the guiding chain 80 extends. In FIG. 17, the connection of the guiding chain 80 at the bearing part 44 and the bearing part 78 is shown in cross-section. The bearing part 44 is mounted to the base frame 30, for instance in the central portion 34 thereof. The bearing part 44 is hingedly mounted to a bearing seat 200 of the base frame 30 via a bearing 198. The bearing part 78 is coupled to the bearing seat 178 of the sensor housing 68 via the bearing 184. The guiding chain 80 that is arranged as a bend-resistant chain ensures that the axes of the bearings 184, 198 are basically oriented in the same plane.

Accordingly, the sensor housing 68 may also act as a reference for the rotation orientation of the guiding shaft 60 and/or the instruments 14 with respect to the Z-axis. Depending on the actual swivel position (pivot movement about the X-axis and/or about the Y-axis) of the shaft 60, a tilting angle between the bearings 184, 198 may be different. However, due to the guiding chain 80 it is ensured that the bearings 184, 198 are retained in the common plane (and/or within a defined tolerance range). In accordance with the embodiment shown in FIG. 17, the guiding shaft 60 that is mounted to the central element 52 and the third drive mount 62 to which the third drive 92 is assigned may freely rotate about the longitudinal axis of the guiding shaft 60 (which is referred to herein for the sake of simplicity as Z-axis).

Figure 18:
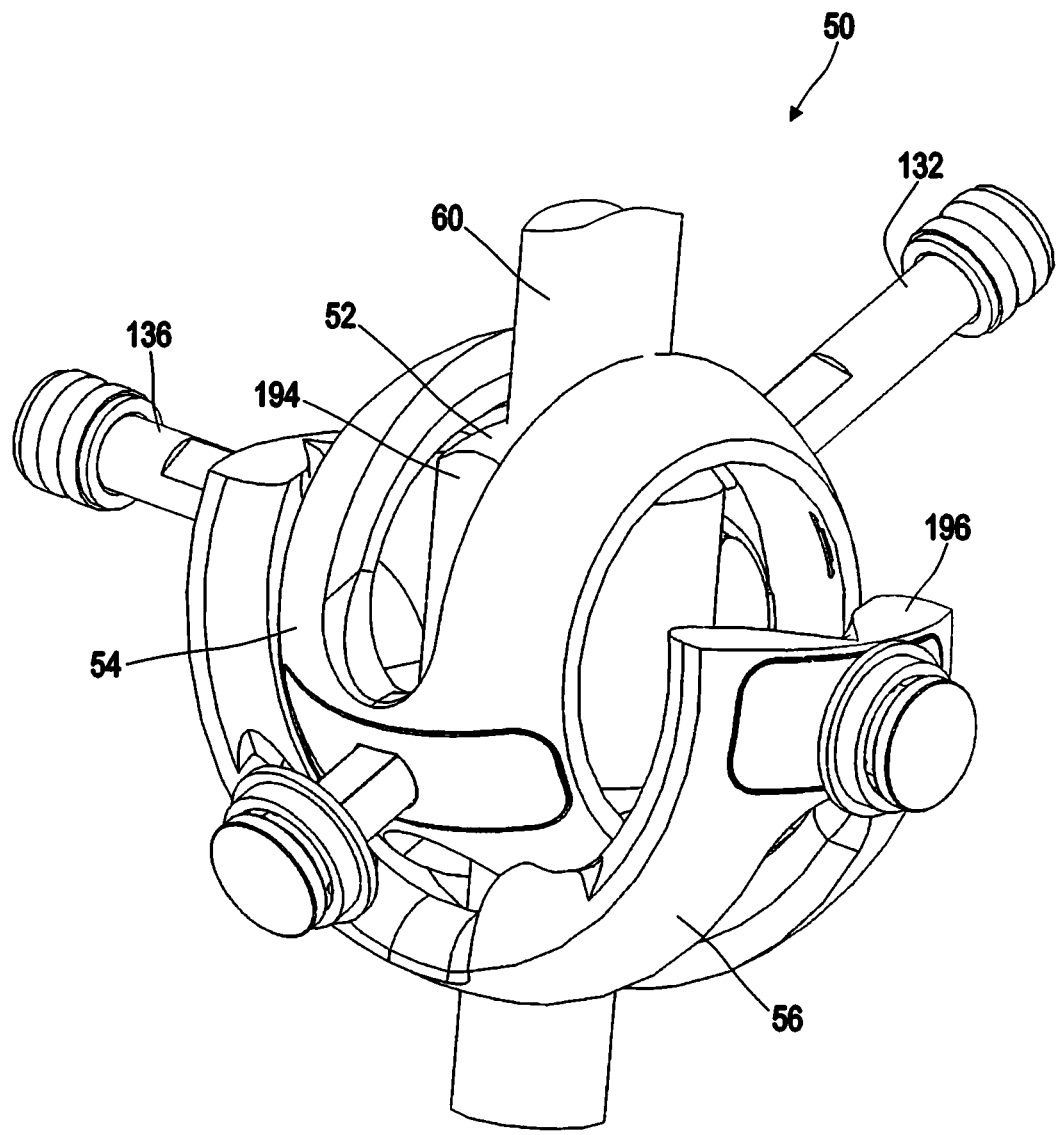
FIG. 18 is a perspective partial view of an alternative embodiment of a joint assembly that may be used for the arrangement according to FIG. 1.

FIG. 18 elucidates a modified embodiment of joint assembly 50 that is arranged to be used in a guiding device 12 of an instrument holder 10. In regard of the generally ball-shaped joint design of the joint assembly 50, additional reference is made to the FIGS. 7 to 9.

By way of example, the central element 52 and the outer element 56 are arranged in FIG. 18 as spherical segments and/or spherical shell segments. Embodiments of this kind are also covered by the scope of the present disclosure. The central element 52 comprises a recess 194 that trims the spherical shape. The outer element 56 comprises a recess 196 that interrupts the annular shape. Nevertheless, also the central element 52 and the outer element 56 comprise in those areas that are arranged to contact further spherically shaped guiding elements with spherical surfaces or spherical segment surfaces to enable the relative movement and/or relative pivot movement of the guiding elements.

The arrangement in accordance with FIG. 18 may result in a reduction of the manufacturing effort, the material effort and the weight of the joint assembly 50. However, also the joint assembly 50 in accordance with FIG. 18 may be at least partially manufactured in an integral, particular an additive fashion. By way of example, the intermediate element 54 may not be easily detached from the central element 52. In addition, the outer element 56 may enclose and/or surround the intermediate element 54 in such a way that a detachment without damaging the parts is not possible. At least two of the three guiding elements 52, 54, 56, and, in some embodiments, all the three guiding elements 52, 54, 56 are integrally manufactured.

FIG. 19 shows a modified embodiment of an instrument holder 10 that is provided with a guiding device 12, wherein the guiding device 12 is basically arranged similar to the guiding device described with reference to FIGS. 1 to 17. This may apply to the design of the joint assembly 50. The guiding device 12 according to FIG. 19 also comprises a guiding shaft 60 that is arranged for receiving a shaft 16 of an instrument 14. For illustrative purposes there is further shown in FIG. 19 a sensor designated by 204 that is assigned to the first drive 88. The sensor 204 is configured to detect a pivot movement and/or a swivel position of the joint assembly 50 and/or of the instrument 14 that is mounted thereto with respect to the X-axis. By way of example, the sensor 204 may be interposed between the transmission shaft 132 and the first drive 88.

As already described herein before, a toothed rod like toothing 160 is at least partially provided at the shaft 16 which is engaged by a gear wheel 158 that is coupled to a third drive 92. The third drive may also be referred to as translational drive, refer to the double arrow 98 in FIG. 19.

The guiding device 12 that is illustrated with reference to FIG. 19 further comprises a fourth drive 206 that may also be referred to as rotation drive (rotation about the Z-axis). The rotation drive 206 is mounted to a drive housing 208 that is assigned to the guiding unit 66. The sensor housing 88 and the drive housing 208 are coupled to one another in a torque-proof fashion. Hence, the guiding chain 80 that is merely schematically shown in FIG. 19 in a broken view prevents also the drive housing 208 from a rotation about the Z-axis. Hence, with respect to the Z-axis, the fourth drive 206 is thus stationary mounted. The fourth drive 206 comprises a pinion 210 that engages a wheel 212 that is mounted to the guiding shaft 60. The wheel 212 is coupled to the guiding shaft 60 in a torque-proof fashion. In other words, driving the wheel 212 by the pinion 210 effects a rotation of the guiding shaft 60 about the Z-axis. The third drive 92 and the instrument 14 that is arranged in the guiding shaft 60 are jointly rotated with the guiding shaft 60 about the Z-axis.

In accordance with the embodiment elucidated with reference to FIG. 19, the guiding device 12 comprises a separate drive for each of its four movement axes (and/or for each of its four degrees of freedom). Accordingly, for each of the degrees of freedom of movement, a force feedback and/or an automated drive may be provided. This may open further fields of application for the instrument holder 10 that is provided with the guiding device 12.

FIG. 20 shows a schematical, greatly simplified partial cross-sectional view the spherical joint assembly 50. As already elucidated herein before, the joint assembly 50 comprises a central element 52, an intermediate element 54 and an outer element 56 that are aligned concentrically with respect to one another. The outer element 56 surrounds the intermediate element 54. The intermediate element 54 surrounds the central element 52. Between the central element 52 and the intermediate element 54, a contact area 220 is formed. Between the intermediate element 54 and the outer element 56, a contact area 222 is formed.

According to at least some embodiments of the present disclosure, the central element 52, the intermediate element 54 and the outer element 56 of the joint assembly 50 are jointly integrally manufactured through an additive manufacturing procedure. Accordingly, due to manufacturing conditions, in the contact areas 220, 222, defined clearances have to be provided, as otherwise simply no joint manufacture of separate parts would be possible. All effort, to ensure a high guiding accuracy (rattle-free, little play, etc.) when in operation, the contact areas 220, 222 are at least sectionally provided with protrusions 216, 218, for instance with nubs and such like.

In the embodiment in accordance with FIG. 20, the contact surface 140 of the central element 52 is provided with a first protrusion 216. Further, the contact surface 144 of the intermediate element 54 is provided with second protrusions 218. In other words, the outer contact surfaces 140, 144 of the central element 52 and/or the intermediate element 56 are at least partially provided with nubs. It is understood that the protrusions 216, 218 basically may also be formed at the opposite contact surfaces 142, 146 that are provided at the intermediate element 54 and/or at the outer element 56. Other combinations may be envisaged. The protrusions 216, 218 increase the guiding accuracy and reduce the guiding play. The protrusions 216, 218 may be jointly manufactured with the guiding elements 52, 54, 56 in an integral, additive fashion. The protrusions 216, 218 form only very little contact areas with the neighboring guiding elements 54, 56.

By way of example, the guiding elements 52, 54, 56 may be manufactured such that the protrusions 216, 218 (in the actually manufactured state) contact the neighboring guiding elements 54, 56 not at all or only minimally (in terms of a firmly bonded contact). In case an actual connection between the guiding elements 52, 54, 56 through their protrusions 216, 218 is generated in the integral joint manufacture, the connection may be released by a relative movement between single ones of the guiding elements 52, 54, 56.

Figure 21:
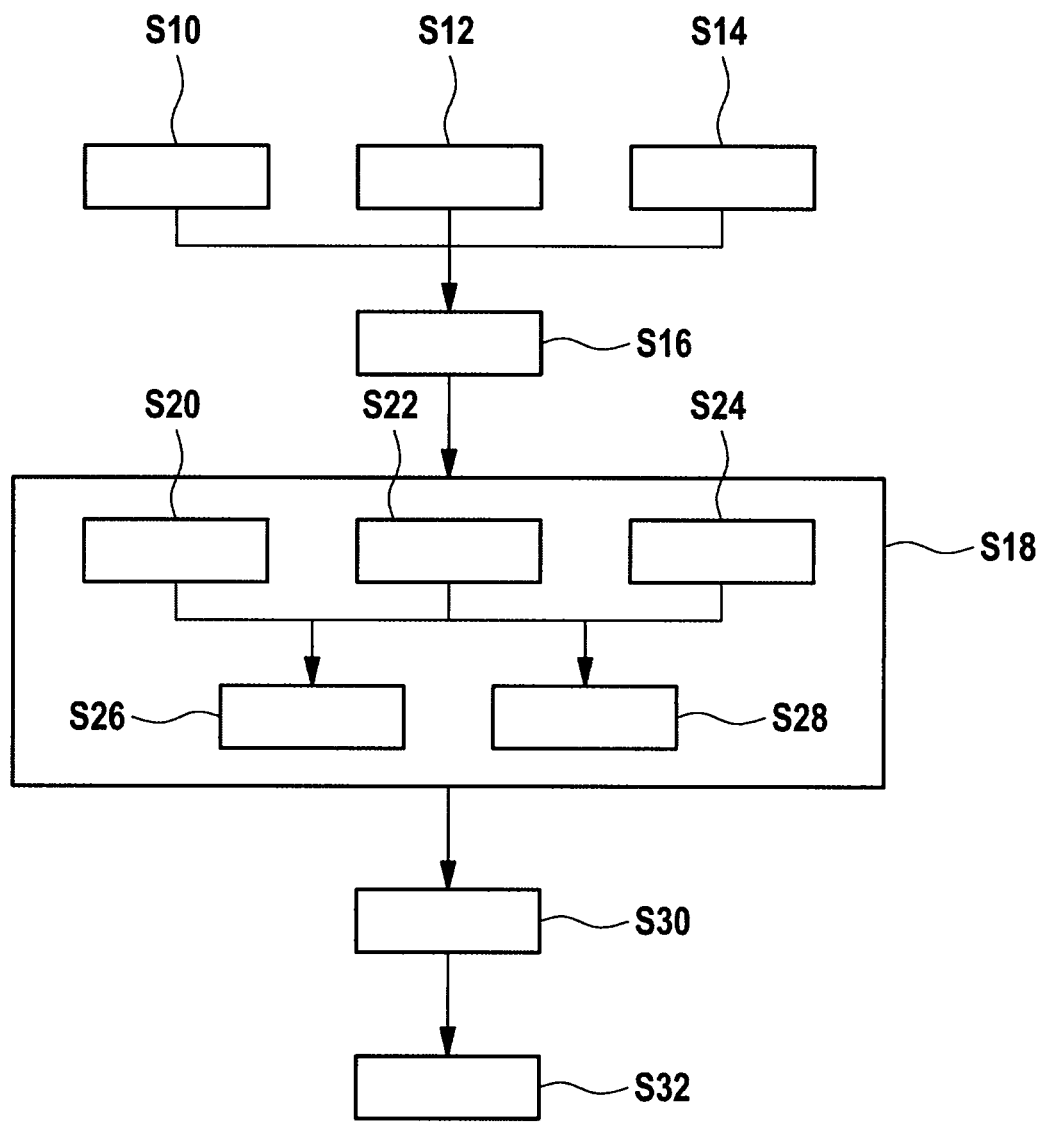
FIG. 21 is a schematic block diagram of an exemplary embodiment of a method for manufacturing a joint assembly involving a spherical guiding element.

With reference to FIG. 21 illustrating a schematic block diagram, an embodiment of a method for manufacturing a spherical joint assembly for a multi-axis guiding device will be elucidated.

The method comprises step S10, S12 and S14 involving designing a joint assembly comprising guiding elements that are nested in one another and arranged concentrically to one another. The step S10 comprises designing a central element. The step S12 comprises designing an intermediate element. The step S14 comprises designing an outer element. A step S16 follows which includes the provision of a (computer-based) model of the joint assembly and the transfer of the model to an apparatus for additive manufacturing.

In a subsequent manufacturing step S18, the joint assembly is additively manufactured. The step S18 comprises (sub)steps S20, S22 and S24 that are at least temporarily performed simultaneous. The step S20 relates to the manufacture of the central element. The step S22 relates to the manufacture of the intermediate element. The step S24 relates to the manufacture of the outer element.

The step S18 further comprises (sub)steps S26 and S28 that relate to the formation of contact areas between the guiding elements of the joint assembly. The step S26 involves the generation of a contact area between the central element and the intermediate element. The step S28 involves the formation of a contact area between the intermediate element and the outer element. In some embodiments, the steps S26 and S28 involve the generation of a plurality of nubby protrusions in the contact areas between the central element, the intermediate element and the outer element. Hence, the central element, the intermediate element and the outer element are, on the one hand, sufficiently spaced away from one another to facilitate the joint manufacture of the (separate) single pieces. Nevertheless, by means of the nubby protrusions, a reduction of the clearance between the guiding elements may be achieved. It is understood that the steps S26 and S28 may at least temporarily take place simultaneous to the steps S20, S22 and S24.

A step S30 involving handling the actually manufactured joint assembly follows the step S18. By way of example, in case the protrusions formed in the steps S26 and S28 at least partially contact the respectively neighboring guiding element, the step S30 may involve a separation of the guiding elements from one another to make them pivotable with respect to one another. The step S30 may further involve a postprocessing.

A further step S32 involving an arrangement and alignment of the joint assembly in a guiding device follows the step S32. To this end, the guiding elements, at least the intermediate element and the outer element, are brought into a defined operation orientation. In this way, for instance, guiding recesses that are formed in the intermediate element and the outer element may be brought into a defined relative orientation. Further, the central element may be coupled to a guiding shaft that at least partially extends through the guiding recesses of the intermediate element and the outer element. In this way, the joint assembly as a whole may be transferred to the desired operation configuration in which the joint assembly, similar to a gimbal bearing, provides two defined pivot axes for the guiding shaft that is mounted to the central element and/or for an instrument that is arranged in the guiding shaft.

The joint assembly including the guiding recesses, further apertures and the nubby protrusions between the single guiding elements may simply be manufactured in an integral, single-piece and additive fashion. In this way, the manufacturing effort may be considerably reduced. The assembly effort may be reduced, as the guiding elements are, in some respect, already assembled to one another when the additive manufacturing is terminated.

What is claimed is:

1. A joint assembly for a multi-axis guiding device for an instrument, comprising:
    first and second guiding elements that are arranged concentrically, and that are, at least sectionally, spherically shaped;
    wherein the first and second guiding elements are integrally manufactured;
    wherein the first and second guiding elements are pivotably coupled to one another;
    wherein the first and second guiding elements are configured such that an outer contact surface of the first guiding element contacts an inner contact surface of the second guiding element;
    wherein either: (i) the outer contact surface of the first guiding element is provided with a plurality of knobs forming a nubby contact surface, and the inner contact surface of the second guiding element is smooth to allow smooth movement of the nubby contact surface of the first guiding element relative to the inner contact surface of the second guiding element; or (ii) the inner contact surface of the second guiding element is provided with a plurality of knobs forming a nubby contact surface, and the outer contact surface of the first guiding element is smooth to allow smooth movement of the nubby contact surface of the second guiding element relative to the outer contact surface of the first guiding element;
    wherein the first guiding element forms a central element and the second guiding element forms an intermediate element;
    wherein the joint assembly further comprises a third guiding element that forms an outer element; and
    wherein the first, second, and third guiding elements are arranged concentrically and integrally manufactured.

2. The joint assembly of claim 1, wherein the first and second guiding elements are integrally and additively manufactured from a material that is provided to be processed in an additive manufacturing process.

3. The joint assembly of claim 1, wherein the outer element is arranged as a spherical shell and undetachably surrounds the intermediate element, and wherein the intermediate element is arranged as a spherical shell and undetachably surrounds the central element.

4. The joint assembly of claim 1, wherein the central element comprises a central guide opening extending therethrough that is arranged for the insertion of an instrument shaft or a guiding shaft.

5. The joint assembly of claim 1, wherein the intermediate element and the outer element comprise groove-shaped guiding recesses, and wherein at least one guiding recess of the intermediate element and at least one guiding recess of the outer element are angularly offset from one another.

6. The joint assembly of claim 5, wherein the central element is provided with or arranged to be coupled to a guiding shaft that at least partially extends through the groove-shaped guiding recesses of the intermediate element and the outer element.

7. The joint assembly of claim 5, further comprising at least one groove-shaped passage for a transmission axis that is provided at the outer element, wherein the passage is arranged to be coupled with the intermediate element, and wherein the guiding recess and the passage are angularly offset from one another.

8. A multi-axis guiding device for an instrument, comprising:
    a base frame; and
    a joint assembly mounted to the base frame, wherein the joint assembly provides two non-parallel pivot axes and includes:
       first and second guiding elements that are arranged concentrically, and that are, at least sectionally, spherically shaped;
       wherein the first and second guiding elements are integrally manufactured;
       wherein the first and second guiding elements are pivotably coupled to one another;
       wherein the first and second guiding elements are configured such that an outer contact surface of the first guiding element contacts an inner contact surface of the second guiding element; and
       wherein either: (i) the outer contact surface of the first guiding element is provided with a plurality of knobs forming a nubby contact surface, and the inner contact surface of the second guiding element is smooth to allow smooth movement of the nubby contact surface of the first guiding element relative to the inner contact surface of the second guiding element; or (ii) the inner contact surface of the second guiding element is provided with a plurality of knobs forming a nubby contact surface, and the outer contact surface of the first guiding element is smooth to allow smooth movement of the nubby contact surface of the second guiding element relative to the outer contact surface of the first guiding element;
    wherein the guiding device further comprises a guiding shaft that is coupled to first guiding element of the joint assembly and that forms a linear guide for the instrument.

9. The guiding device as claimed in claim 8, wherein the guiding shaft and the first guiding element further define a rotation axis for the instrument.

10. The guiding device of claim 8, further comprising a translational actuator that is coupled to the guiding shaft and that is configured to engage an instrument shaft of the instrument that is inserted in the guiding shaft for translational force transmission.

11. The guiding device of claim 8, further comprising a rotation drive that is coupled to the guiding shaft and that is configured to mediately or directly engage the instrument shaft that is inserted in the guiding shaft for rotatory force transmission.

12. The guiding device of claim 8, wherein the guiding shaft is coupled to the base frame via a guiding unit, wherein the guiding unit is coupled with a rotation prevention feature.

13. The guiding device of claim 12, wherein the rotation prevention feature involves a guiding chain that forms a hinged connection between the base frame and the guiding unit.

14. The guiding device of claim 8, further comprising a sensor unit that is assigned to the guiding shaft, wherein the sensor unit is arranged to detect a translational movement and a rotation movement of an inserted instrument, and wherein the sensor unit is multi-dimensionally operative.

15. A multi-axis guiding device for an instrument, comprising:
a base frame; and
a joint assembly mounted to the base frame, wherein the joint assembly provides two non-parallel pivot axes and includes:
first and second guiding elements that are arranged concentrically, and that are, at least sectionally, spherically shaped;
wherein the first and second guiding elements are integrally manufactured;
wherein the first and second guiding elements are pivotably coupled to one another;
wherein the first and second guiding elements are configured such that an outer contact surface of the first guiding element contacts an inner contact surface of the second guiding element; and
wherein either: (i) the outer contact surface of the first guiding element is provided with a plurality of knobs forming a nubby contact surface, and the inner contact surface of the second guiding element is smooth to allow smooth movement of the nubby contact surface of the first guiding element relative to the inner contact surface of the second guiding element; or (ii) the inner contact surface of the second guiding element is provided with a plurality of knobs forming a nubby contact surface, and the outer contact surface of the first guiding element is smooth to allow smooth movement of the nubby contact surface of the second guiding element relative to the outer contact surface of the first guiding element;
wherein the guiding device further comprises a first pivot actuator for a first pivot axis that is coupled to the second guiding element of the joint assembly, a second pivot actuator for the second pivot axis that is coupled to an outer element of the joint assembly,
wherein the first pivot actuator is coupled via a transmission axis to the second guiding element, and wherein the transmission axis extends through the outer element.

16. A joint assembly for a multi-axis guiding device for an instrument, comprising:
first and second guiding elements that are arranged concentrically, and that are, at least sectionally, spherically shaped;
wherein the first and second guiding elements are integrally manufactured;
wherein the first and second guiding elements are pivotably coupled to one another;
wherein the first and second guiding elements are configured such that an outer contact surface of the first guiding element contacts an inner contact surface of the second guiding element;
wherein either: (i) the outer contact surface of the first guiding element is provided with a plurality of knobs forming a nubby contact surface, and the inner contact surface of the second guiding element is smooth to allow smooth movement of the nubby contact surface of the first guiding element relative to the inner contact surface of the second guiding element; or (ii) the inner contact surface of the second guiding element is provided with a plurality of knobs forming a nubby contact surface, and the outer contact surface of the first guiding element is smooth to allow smooth movement of the nubby contact surface of the second guiding element relative to the outer contact surface of the first guiding element;
wherein the joint assembly further comprises a third guiding element;
wherein the first, second, and third guiding elements are arranged concentrically relative to one another, and are, at least sectionally, spherically shaped;
wherein the first, second, and third guiding elements form components of a combined spherical bearing and comprise spherical contact areas;
wherein the first, second, and third guiding elements are integrally manufactured; and
wherein the first, second, and third guiding elements are pivotably coupled to one another; and
wherein at least two of the first, second, and third guiding elements include respective nubby contact surfaces.

17. The joint assembly of claim 16, wherein the first, second, and third guiding elements are integrally manufactured in a loss-proof manner.

18. The joint assembly of claim 16, wherein the first, second, and third guiding elements are undetachable from one another.

19. A joint assembly for a multi-axis guiding device for an instrument, comprising:
first and second guiding elements that are arranged concentrically, and that are, at least sectionally, spherically shaped;
wherein the first and second guiding elements are integrally manufactured;
wherein the first and second guiding elements are pivotably coupled to one another;
wherein the first and second guiding elements are configured such that an outer contact surface of the first guiding element contacts an inner contact surface of the second guiding element;
wherein either: (i) the outer contact surface of the first guiding element is provided with a plurality of knobs forming a nubby contact surface, and the inner contact surface of the second guiding element is smooth to allow smooth movement of the nubby contact surface of the first guiding element relative to the inner contact surface of the second guiding element; or (ii) the inner contact surface of the second guiding element is provided with a plurality of knobs forming a nubby contact surface, and the outer contact surface of the first guiding element is smooth to allow smooth movement of the nubby contact surface of the second guiding element relative to the outer contact surface of the first guiding element;
wherein the joint assembly further comprises a third guiding element arranged concentrically with the first and second guiding elements;
wherein the third guiding element at least partially surrounds the second guiding element.

20. The joint assembly of claim 19, wherein either: (i) an outer contact surface of the second guiding element is provided with a plurality of knobs forming a nubby contact surface, and an inner contact surface of the third guiding element is smooth to allow smooth movement of the nubby contact surface of the second guiding element relative to the inner contact surface of the third guiding element; or (ii) the inner contact surface of the third guiding element is provided with a plurality of knobs forming a nubby contact surface, and the outer contact surface of the second guiding element is smooth to allow smooth movement of the nubby contact surface of the third guiding element relative to the outer contact surface of the second guiding element.

* * * * *